United States Patent
Mizrahi et al.

(10) Patent No.: US 11,633,434 B2
(45) Date of Patent: Apr. 25, 2023

(54) TOPICAL KITS AND COMPOSITIONS AND USE THEREOF

(71) Applicant: TECHNION RESEARCH & DEVELOPMENT FOUNDATION LIMITED, Haifa (IL)

(72) Inventors: Boaz Mizrahi, Haifa (IL); Maayan Lufton, Kiryat Yam (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 275 days.

(21) Appl. No.: 16/645,480

(22) PCT Filed: Sep. 6, 2018

(86) PCT No.: PCT/IL2018/051012
§ 371 (c)(1),
(2) Date: Mar. 8, 2020

(87) PCT Pub. No.: WO2019/049150
PCT Pub. Date: Mar. 14, 2019

(65) Prior Publication Data
US 2020/0215124 A1 Jul. 9, 2020

Related U.S. Application Data

(60) Provisional application No. 62/555,105, filed on Sep. 7, 2017.

(51) Int. Cl.
| | | |
|---|---|---|
| *C12N 1/00* | (2006.01) | |
| *A61K 35/74* | (2015.01) | |
| *A61P 31/10* | (2006.01) | |
| *A61K 8/99* | (2017.01) | |
| *A61K 9/00* | (2006.01) | |
| *A61Q 17/00* | (2006.01) | |
| *A61Q 19/00* | (2006.01) | |
| *C12N 1/20* | (2006.01) | |
| *A61K 9/06* | (2006.01) | |
| *A61K 47/10* | (2017.01) | |

(52) U.S. Cl.
CPC ............ *A61K 35/74* (2013.01); *A61K 8/99* (2013.01); *A61K 9/006* (2013.01); *A61K 9/0014* (2013.01); *A61K 9/06* (2013.01); *A61K 47/10* (2013.01); *A61P 31/10* (2018.01); *A61Q 17/005* (2013.01); *A61Q 19/00* (2013.01); *C12N 1/20* (2013.01); *A61K 2800/24* (2013.01); *A61K 2800/48* (2013.01); *A61K 2800/88* (2013.01)

(58) Field of Classification Search
CPC ..................................................... A61K 35/74
See application file for complete search history.

(56) References Cited

U.S. PATENT DOCUMENTS

| | | |
|---|---|---|
| 6,261,577 B1 | 7/2001 | Kessler |
| 2007/0190176 A1* | 8/2007 | Percival ............... A61K 33/18 |
| | | 424/661 |
| 2013/0046275 A1 | 2/2013 | Holzer et al. |
| 2015/0374607 A1 | 12/2015 | Lanzalaco et al. |

FOREIGN PATENT DOCUMENTS

| | | |
|---|---|---|
| CN | 105147723 A | 12/2015 |
| EP | 1629846 A2 | 3/2006 |
| EP | 1736537 A1 | 12/2006 |
| WO | 0113927 A2 | 3/2001 |
| WO | 2014100777 A2 | 6/2014 |
| WO | 2017208172 A1 | 12/2017 |

OTHER PUBLICATIONS

Wu et al (Journal of Materials Chemistry vol. 22, pp. 18596-18602) (Year: 2012).*
Monica A. Garcia-Solache and Arturo Casadevall,, "Global Warming Will Bring New Fungal Diseases for Mammals", Mbio, American Society for Microbiology, vol. 1. Apr. 2010.
S. B. Girois et al., "Adverse effects of antifungal therapies in invasive fungal infections: review and meta-analysis", European Journal of Clinical Microbiology & Infectious Diseases: Official Publication of the European Society of Clinical Microbiology, vol. 25 Issue 2 pp. 138-149, 2006.
Colin J. Ingham et al., "Rapid susceptibility testing and microcolony analysis of *Candida* spp. cultured and imaged on porous aluminum oxide", Plos One, vol. 7 Issue 3 pp. 33818, 2012.
Yuhan Lee et al., "Thermosensitive, injectable, and tissue adhesive sol-gel transition hyaluronic acid/pluronic composite hydrogels prepared from bio-inspired catechol-thiol reaction", Soft Matter, vol. 6 Issue 5 p. 977, 2010.
Ting Yu Liu et al., "Biomedical nanoparticle carriers with combined thermal and magnetic responses", Nano Today, vol. 4 pp. 52-65, Feb. 2009.
Malcolm D. Richardson, "Changing patterns and trends in systemic fungal infections", Journal of Antimicrobial Chemotherapy, vol. 56 pp. 5-11, 2005.
F. Peypoux et al., "Recent trends in the biochemistry of surfactin", Applied Microbiology and Biotechnology, vol. 51 Issue 5 pp. 553-563, Jun. 1999.

(Continued)

*Primary Examiner* — Albert M Navarro
(74) *Attorney, Agent, or Firm* — The Roy Gross Law Firm, LLC; Roy Gross

(57) ABSTRACT

Kits and composition comprising: (i) a thermo-responsive hydrogel characterized by a viscosity suitable for hardening after administration on a subject's skin; (ii) a bacterial growth medium; and optionally, (iii) a population of non-pathogenic viable bacteria, are provided. Methods for topically delivering a therapeutic or cosmeceutical agent such as for inhibiting or reducing growth of microorganisms on a subject's skin are further provided.

12 Claims, 20 Drawing Sheets

(3 of 20 Drawing Sheet(s) Filed in Color)

(56) References Cited

OTHER PUBLICATIONS

Frank C. Roia and Raymond W. Vanderwyk "Resident microbial flora of the human scalp and its relationship to dandruff", Journal of Society of Cosmetic Chemists, 113, 1969.

Zofia S. Olempska-Beer et al., "Food-processing enzymes from recombinant microorganisms—a review", Regulatory Toxicology and Pharmacology, vol. 45 Issue 2 pp. 144-158, Jul. 2006.

Marcus Schallmey et al., "Developments in the use of *Bacillus* species for industrial production" Canadian Journal of Microbiology, vol. 50 Issue 1 pp. 1-17, Feb. 2004.

Lidia Westers et al., "Bacillus subtilis as cell factory for pharmaceutical proteins: a biotechnological approach to optimize the host organism", Biochimica Et Biophysica Acta-Molecular Cell Research, vol. 1694 Issues 1-3 pp. 299-310, 2004.

Daria Julkowska et al., "Comparative analysis of the development of swarming communities of Bacillus subtilis 168 and a natural wild type: critical effects of surfactin and the composition of the medium", J Bacteriol, vol. 187 Issue 1 pp. 65-76, 2005.

Julian C. Gilbert et al., "The effect of solutes and polymers on the gelation properties of pluronic F-127 solutions for controlled drug delivery", Journal of Controlled Release, vol. 5 Issue 2 Sep pp. 113-118, 1987.

M. M. Nakano et al., "Identification of a genetic locus required for biosynthesis of the lipopeptide antibiotic surfactin in Bacillus subtilis", J Bacteriol, vol. 170 Issue 12 pp. 5662-5668, 1988.

Natalia Malfanova et al., "Cyclic lipopeptide profile of the plant-beneficial endophytic bacterium Bacillus subtilis HC8", vol. 194 Issue 11 pp. 893-899, May 2012.

Xiangyang Liu et al., "Optimization for the Production of Surfactin with a New Synergistic Antifungal Activity", PLoS One, vol. 7 issue 5 e34430, May 2012.

P. Biniarz et al., "The lipopeptides pseudofactin II and surfactin effectively decrease Candida albicans adhesion and hydrophobicity", Antonie van Leeuwenhoek, vol. 108 Issue 2 pp. 343-353, 2015.

Hélène Cawoy et al., "Lipopeptides as main ingredients for inhibition of fungal phytopathogens by Bacillus subtilis/amyloliquefaciens", Microb Biotechnol, 2015, vol. 8 Issue 2 pp. 281-295.

N. Vanittanakom et al., "Fengycin—a novel antifungal lipopeptide antibiotic produced by Bacillus subtilis F-29-3", J Antibiot (Tokyo), vol. 39 Issue 7 pp. 888-901, 1986.

L. Thimon et al., "Effect of the lipopeptide antibiotic, iturin A, on morphology and membrane ultrastructure of yeast cells", Fems Microbiology Letters, vol. 128 Issue 2 pp. 101-106, May 1995.

H. Razafindralambo et al., "Surface-Active Properties of Surfactin/Iturin A Mixtures Produced by Bacillus subtilis", Langmuir, vol. 13 Issue 23 pp. 6026-6031, 1997.

Wing Cheung Mak et al., "Triggering of drug relase of particles in hair follicles", Journal of Controlled Release, vol. 160 pp. 509-514, 2012.

B. L. Hahn and P. G. Sohnle "Characteristics of dermal invasion in experimental cutaneous candidiasis of leucopenic mice", vol. 91 Issue 3 pp. 233-237, 1988.

C. Valenta and B. G. Auner, "The use of polymers for dermal and transdermal delivery", European Journal of Pharmaceutics and Biopharmaceutics, vol. 58 Issue 2 pp. 279-289, 2004.

Tacito Graminha Campois et al.,"Immunological and histopathological characterization of cutaneous candidiasis", Journal of Medical Microbiology, vol. 64 Issue 8, pp. 810-817, 2015.

Heather R. Conti et al., "Animal Models for Candidiasis", Current Protocols in Immunology, vol. 105 Issue 1 pp. 19.6.1-19.6.17, 2014.

Cynthia Shackelford et al., "Qualitative and quantitative analysis of nonneoplastic lesions in toxicology studies", Toxicol Pathol, vol. 30 Issue 1 pp. 93-96, 2002.

Palashpriya Das et al., "Genetic regulations of the biosynthesis of microbial surfactants: an overview", Biotechnol Genet Eng Rev, vol. 25 pp. 165-185, 2008.

Tse Siang Kang and Raymond C Stevens, "Structural aspects of therapeutic enzymes to treat metabolic disorders", Hum Mutat, vol. 30 Issue 12 pp. 1591-1610, 2009.

Sindhu Abraham et al., "Sustained ophthalmic delivery of ofloxacin from an ion-activated in situ gelling system" Pakistan Journal of Pharmaceutical Sciences, vol. 22 issue 2 pp. 175-179, 2009.

Yan Zhi et al., "Genome and transcriptome analysis of surfactin biosynthesis in Bacillus amyloliquefaciens MT45", Scientific Reports vol. 7:40976, 2017.

Hu Jin et al., "Continuous enhancement of iturin A production by Bacillus subtilis with a stepwise two-stage glucose feeding strategy", BMC Biotechnol, vol. 15 Issue 53, 2015.

Gun Wirtanen et al: "Efficacy testing of commercial disinfectants against foodborne pathogenic and spoilage microbes in biofilm-constructs", Eur Food Res Technol (2001) 213:409-414.

Karima Bertal et al.: "Antimicrobial activity of novel biocompatible wound dressings based on triblock copolymer hydrogels", J Mater Sci (2009) 44:6233-6246.

Database WPI, Week 201638, Thomson Scientific, London, GB; AN 2016-014622, XP002802846, 2017.

PCT Search Report for International Application No. PCT/IL2018/051012 dated Dec. 23, 2018, 6 pp.

PCT Written Opinion for International Application No. PCT/IL2018/051012 dated Dec. 23, 2018, 5 pp.

PCT Preliminary Report on Patentability for International Application No. PCT/IL2018/051012 dated Mar. 10, 2020, 6 pp.

\* cited by examiner

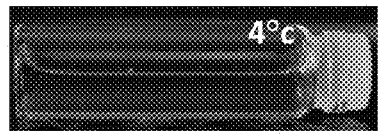
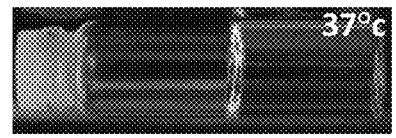
Figure 2A
Figure 2B
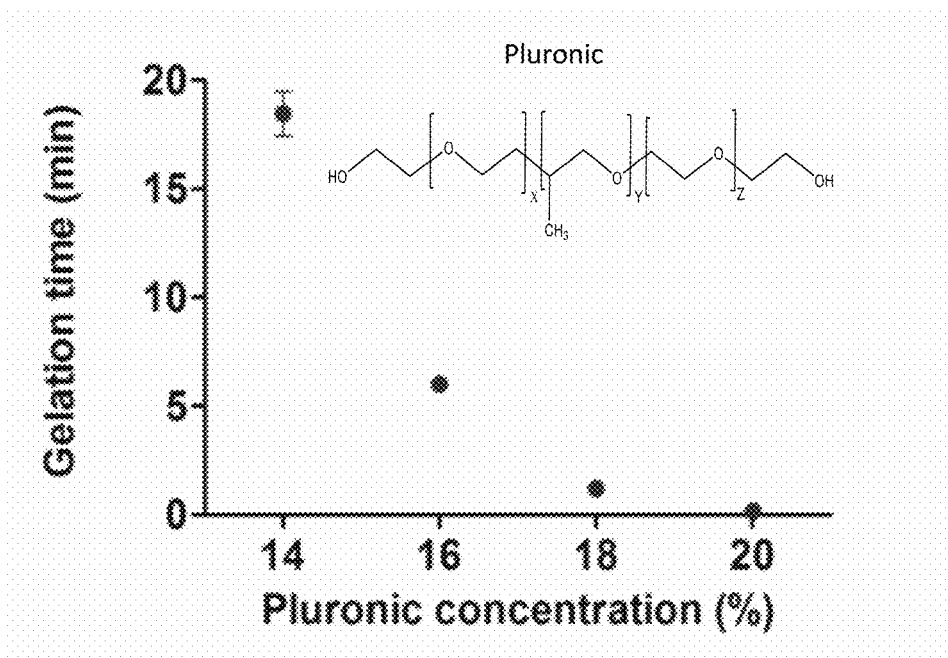
Figure 2C

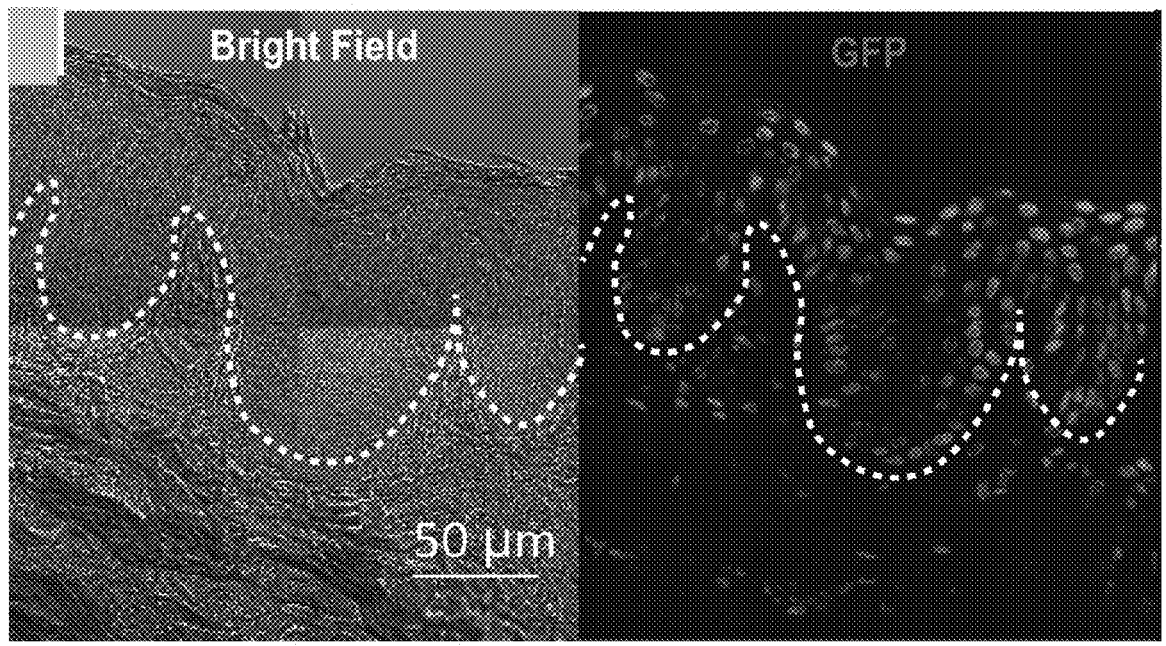
Figure 4C
Figure 4D
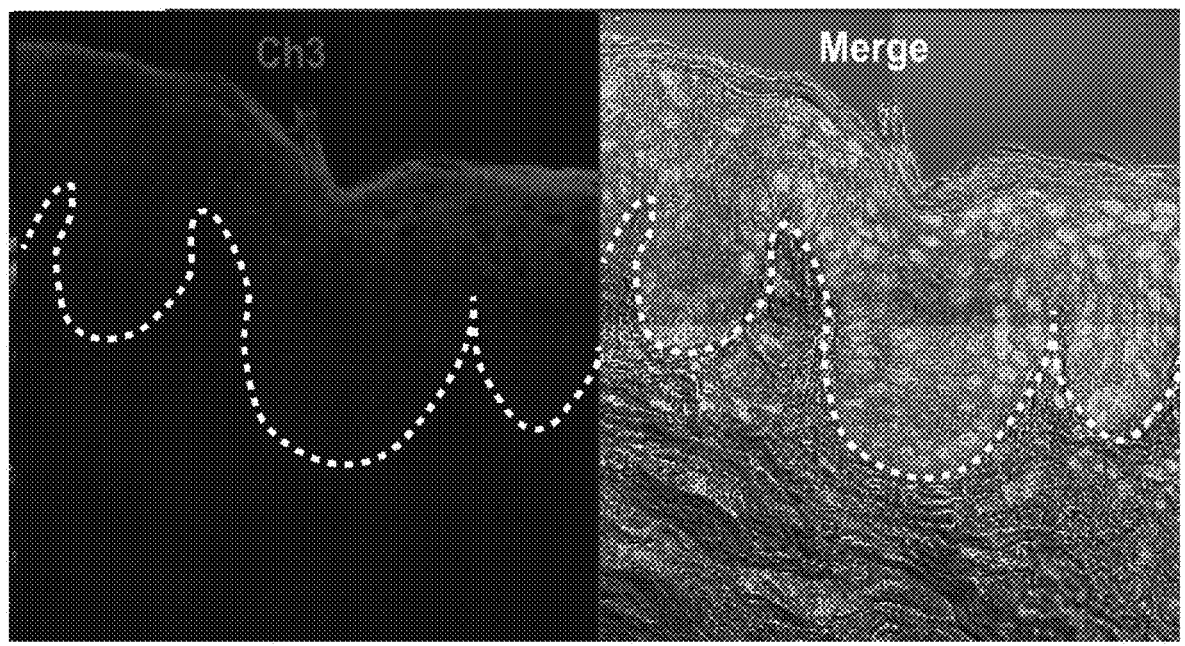
Figure 4E
Figure 4F

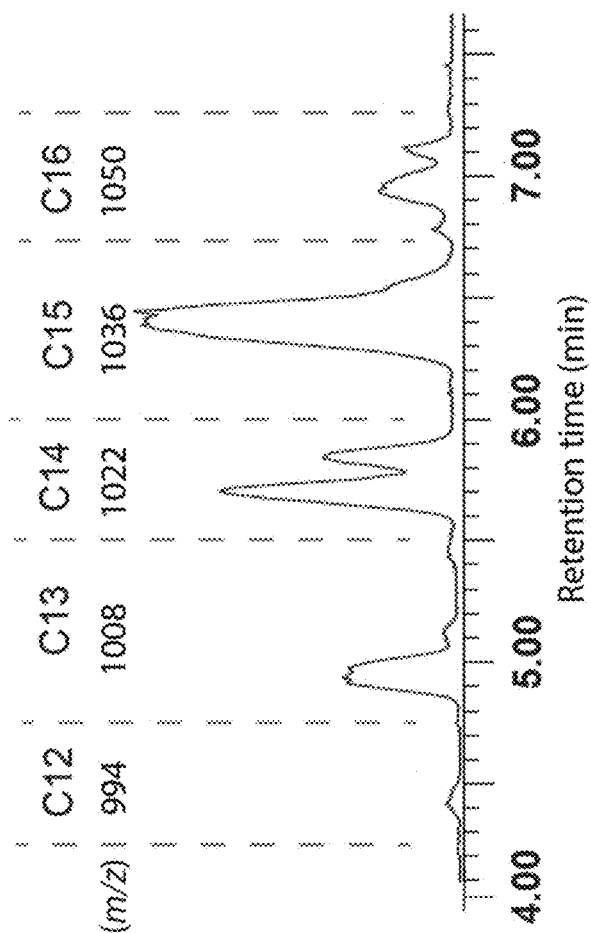
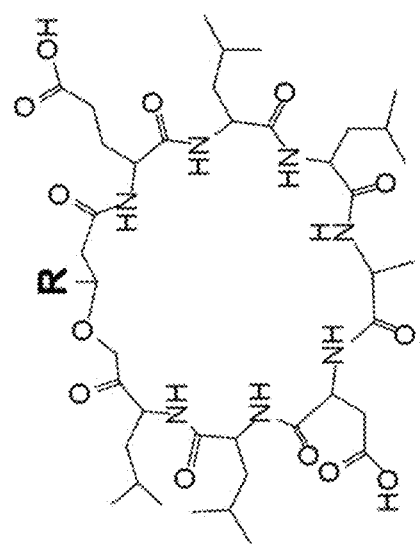
R = C12, C13, C14, C15, C16
Figure 12A
Figure 12B

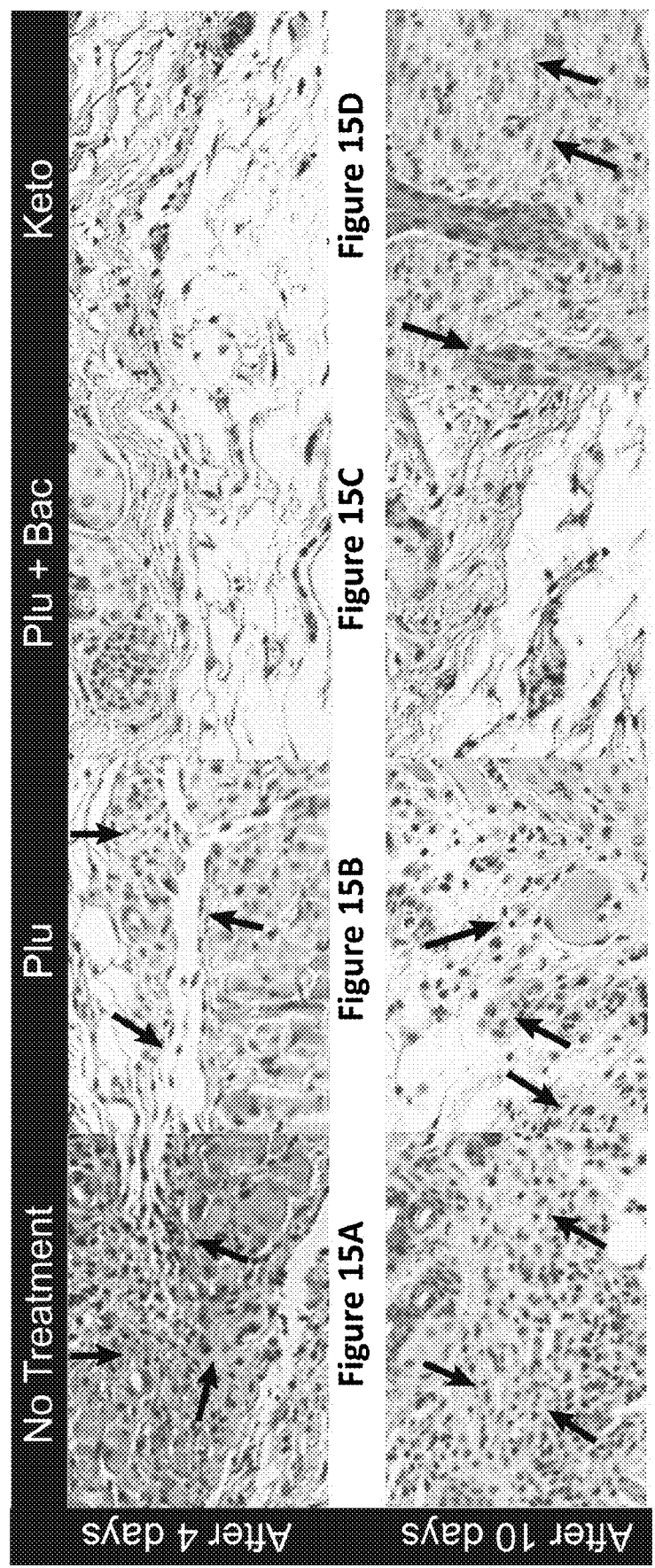

TOPICAL KITS AND COMPOSITIONS AND USE THEREOF

CROSS-REFERENCE TO RELATED APPLICATIONS

This application is a National Phase of PCT Patent Application No. PCT/IL2018/051012 having International filing date of Sep. 6, 2018, which claims the benefit of priority of U.S. Provisional Patent Application No. 62/555,105, filed on Sep. 7, 2017. The contents of the above applications are all incorporated by reference as if fully set forth herein in their entirety.

FIELD OF THE INVENTION

The present invention is in the field of material science and relates, inter alia, to the field of inverse-freezing materials including but not limited to the topical application of bacteria having a therapeutic effect.

BACKGROUND OF THE INVENTION

A reverse-freezing material is a material that increases its viscosity with applied heat and/or rise in temperature (upon a certain temperature range), without apparent loss of solvent. The increase in viscosity can be of a few percent, or of tens or hundreds of percent. Inverse-freezing materials can be found in literature also under the names "reverse-melting", "thermo-gelating", "thermo-solidifying" and others. A field in which reverse thermo-gelating materials have found prolific uses is biology and medicine, and examples for applications include injectable and controlled drug delivery systems, ophthalmic solutions and applicators, and in situ generated implants or plugs.

Fungal infections are a significant and growing public health concern infecting billions of people every year. Most people will suffer from fungal infections in their lifetimes. Several reasons have been proposed for this increase including population aging and the increase of patients receiving immunosuppressive or broadspectrum antibiotics. Emergence of HIV, influenza virus, cancer and global warming have been attributed to be another cause of emergence of fungal infections.

More than 17 different *Candida* species are known to be aetiological agents of human infection; from which the yeast *Candida albicans* is the most frequently encountered cause of infections. The pathogenicity of *Candida* species is attributed to certain virulence factors, such as the ability to evade host defenses, adherence, biofilm formation (on host tissue and on medical devices) and the production of tissue-damaging hydrolytic enzymes such as proteases, phospholipases and haemolysin.

Currently, there are two main pharmacological anti-fungal treatments approved by the US Food and Drug Administration (FDA): (1) Amphotericin B. This drug is considered the "gold standard" of antifungal therapy, however, it has several drawbacks, including the necessity of intravenous administration; intolerance by many patients due to unpleasant side effects (e.g. fever, chills and headache) and more important, it is associated with significant liver and kidney toxicities that limit its use. (2) Azoles, this group of antifungal agents has added greatly to the therapeutic options for treatment of fungal infections. Many problems are associated with this family: clotrimazole for example, can only be administered as a topical or troche preparation while other members have multiple toxic effects, especially on the hematologic system, skin, and heart. Moreover, an increase in the number of *Candida* strains resistant to antifungal drugs, associated with parallel increase in the maturation process was recognized worldwide. This increase in resistant strains along with drawbacks of current treatments necessitates a search for new therapeutic strategies for local fungal infection.

SUMMARY OF THE INVENTION

According to some embodiments of the present invention, there is provided a kit comprising: (i) a material characterized by a viscosity that is less than about 1 Pa, or, in some embodiments, less than 5 Pa or, in some embodiments, less than 10 Pa under a first stimulus, and a viscosity that is higher than about 30, 40, 50, 60, 70, 80, 90 or higher than 100 Pa, under a second stimulus, (ii) a bacterial growth medium; and optionally, (iii) a population of non-pathogenic viable bacteria.

In some embodiments, the first stimulus and the second stimulus are selected from the group consisting of temperature, and pH. In some embodiments, the first stimulus is a temperature below 35° C. and the second stimulus is a temperature above 36° C.

In some embodiments, the material is a reverse thermo-responsive material. In some embodiments, the material is characterized by lower critical solution temperatures (LCST). In some embodiments, the material is a polymeric material. In some embodiments, the polymeric material is selected from poly(ethylene oxide)-poly(propylene oxide)-poly(ethylene oxide) (PEO-PPO-PEO) triblocks, random or alternating reverse thermo-responsive PEO-PPO block copolymers, and copolymers comprising PEO and PPO segments. In some embodiments, the polymeric material is polymer is {EO}99-{PO}67-{EO}99 triblock (Pluronic F127).

In some embodiments, the kit comprising a population of non-pathogenic viable bacteria. In some embodiments, the population of the non-pathogenic viable bacteria is selected from a population of non-pathogenic bacteria resident on the skin or a mucous membrane of a mammal. In some embodiments, the non-pathogenic viable bacteria have a therapeutic or cosmetic effect. In some embodiments, the population of non-pathogenic viable bacteria express and/or secret a compound of interest. In some embodiments, the compound of interest has a therapeutic or cosmetic effect. In some embodiments, the compound is selected from an antifungal agent, an antibacterial agent, and an antiviral agent.

In some embodiments, the bacteria are in a dormant form. In some embodiments, the bacteria are selected from the group consisting of *Acinetobacter, Actinomycetales, Anaerococcus, Bacillales, Bifidobacterium, Enhydrobacter, Enterococcus, Finegoldia, Carnobacterium, Coryneobacterium, Lactobacillus, Lactococcus, Leunconostoc, Macrooccus, Micrococcineae, Oenococcus, Pediococcus, Peptoniphilus, Propionibacterium, Salinicoccus, Sphingomonas, Strepococcus, Tetragenoccus,* and *Weissella*. In some embodiments, the bacteria are selected from the group consisting of *Bacillus subtilis, Bacillus uniflagellatus, Bacillus lateropsorus, Bacillus laterosporus* BOD, *Bacillus megaterium, Bacillus polymyxa, Bacillus licheniformis, Bacillus pumilus, Bacillus sterothermophilus, Lactobacillus casei, Lactobacillus reuteri, Lactobacillus acidophilus, Lactobacillus jensenii, Bifidobacterium lognum, Bifidobacterium reuteri, Bifidobacterium lactis, Bifidobacterium breve, Bifidobacterium animalis, Propionibacterium acidipropionici, Propionibacterium freudenreichii, Propionibacterium thoenii,* and *Propionibacterium jensenii*. In some embodiments, the bacteria comprise *Bacillus Subtilis*.

In some embodiments, the kit further comprising instructions for topical application onto a skin or a mucus membrane of a subject. In some embodiments, the kit is being used for inhibiting growth of pathogenic-bacteria, yeast, fungus or virus. In some embodiments, the kit is being used for inhibiting growth of *Candida albicans*. In some embodiments, the growth medium is selected from the group consisting of gel, agar, and broth.

In some embodiments, the kit further comprising an applier, configured to deliver a predefined amount of one or more of components (i) to (iii) to a solution or to a mixture thereof.

According to some embodiments of the present invention, there is provided a pharmaceutical or cosmeceutical composition comprising: (i) a material characterized by a viscosity that is less than about 100 Pa under a first stimulus, and a viscosity that is higher than about 500 Pa under a second stimulus, (ii) bacterial growth medium, and (iii) a population of non-pathogenic viable bacteria.

In some embodiments, the bacteria are at a concentration of $10^7$-$10^9$ bacteria/ml. In some embodiments, the amount of the bacterial growth medium, is in the range of from 50% to 85% (w/v), by total amount of composition.

In some embodiments, the amount of material, is in the range of from 10% (w/v) to 30% (w/v).

According to some embodiments of the present invention, there is provided a method for inhibiting or reducing growth of microorganisms selected from fungus, bacteria, yeast, virus, or a combination thereof, on skin or a mucus membrane of a subject in need thereof, the method comprising contacting the composition described herein with a skin or a mucus membrane of a subject. In some embodiments, the inhibiting or reducing the growth of the microorganisms is affected for at least 1 h upon the contacting. In some embodiments, the concentration of the bacterial growth medium in the composition is selected so as to exhibits gelation after a time duration of 30 sec to 15 min upon the contacting of the composition and the skin or the mucus membrane. In some embodiments, the composition exhibits gelation after a time duration of 30 sec to 15 min upon the contacting.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawing in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
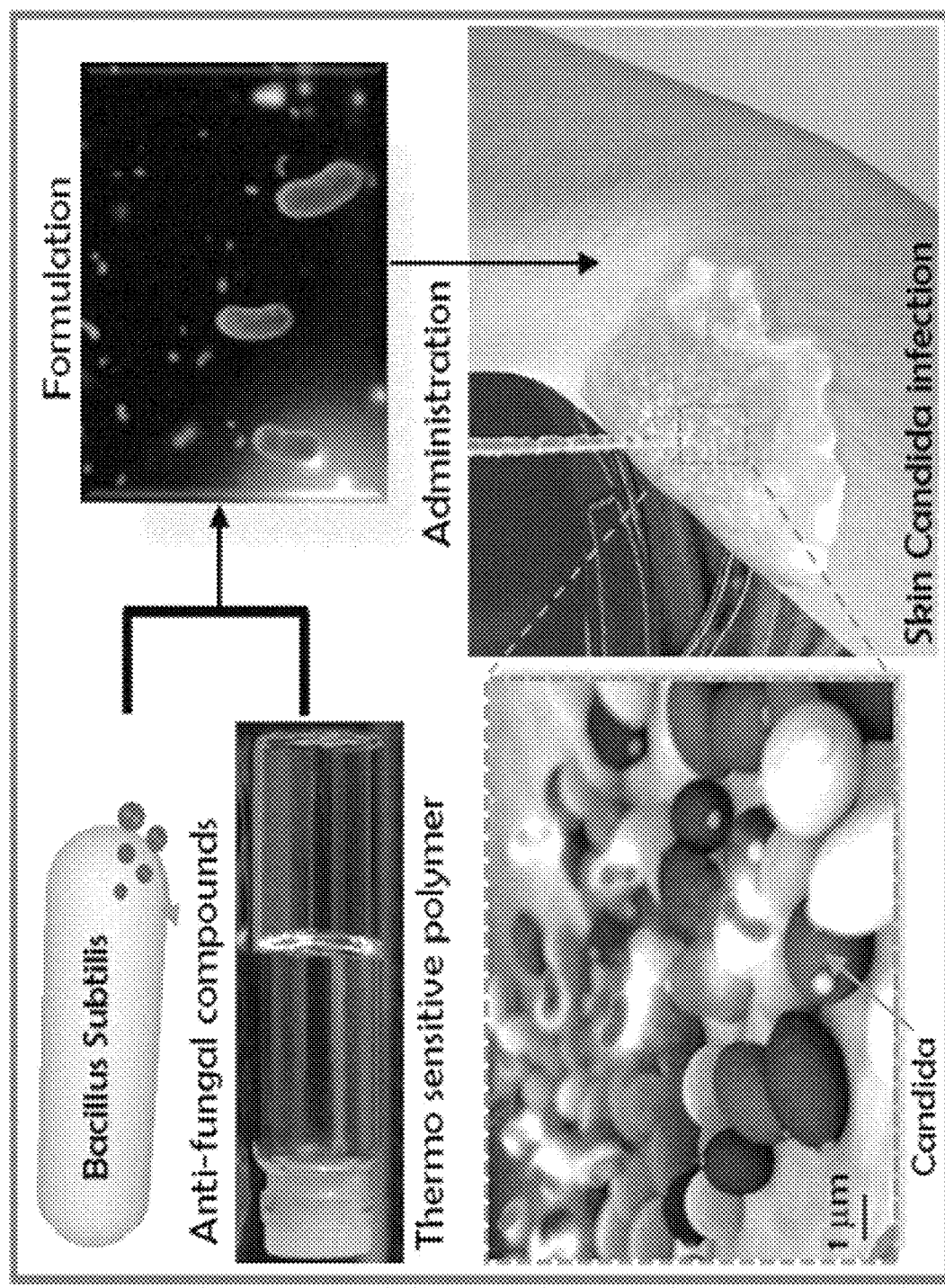

FIG. 1 presents a scheme showing the concept of the disclosed invention in some embodiments thereof: a food-grade bacterium is encouraged to secrete a desired therapeutic protein. Then, bacteria are encapsulated in a suitable polymeric formula that allows germination and proliferation. After administration, the transparent formula will harden and function as a unique "factory" that continuously produces and releases the natural therapeutic proteins (e.g., anti-fungal agents) locally.

Figure 2D:
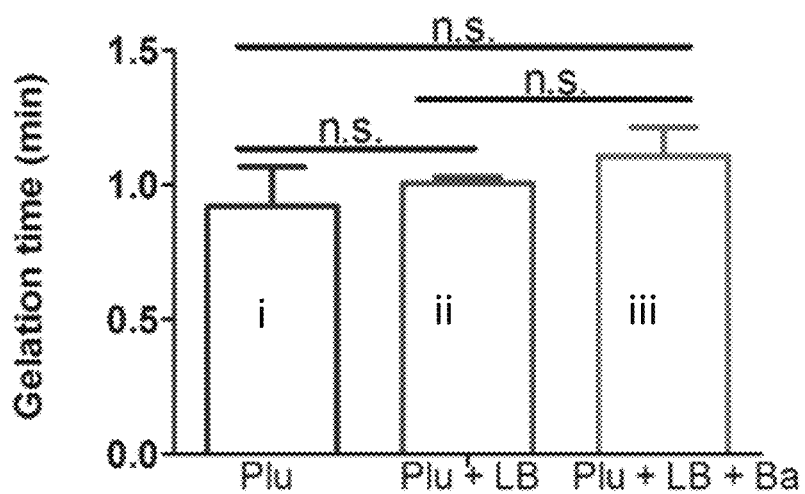
Figure 2E:
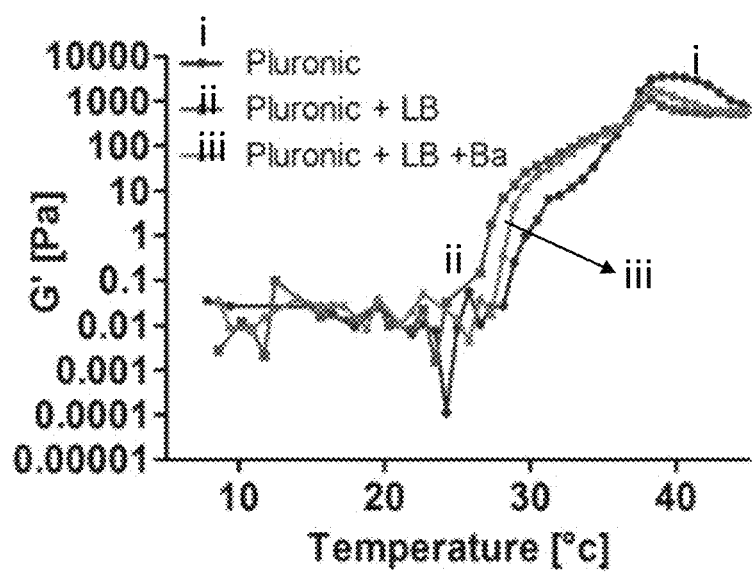

FIGS. 2A-E present gelation properties and characterization of: pluronic (18% w/v) at 4° C. having a liquid form (FIG. 2A), pluronic (18% w/v) having a gel form at 37° C. (FIG. 2B), Gelation time (min) Vs pluronic concentration (FIG. 2C) when heated from room temperature to 37° C., G' as a function of temperature for different compositions: pluronic (18% w/v), pluronic+LB (10:1), pluronic+LB+bacillus subtilis (10:1) (1 rad·s$^{-1}$, 1% strain) (FIG. 2D), and Gelation time (min) for the corresponding solution of FIG. 2D (FIG. 2E).

Figure 3:
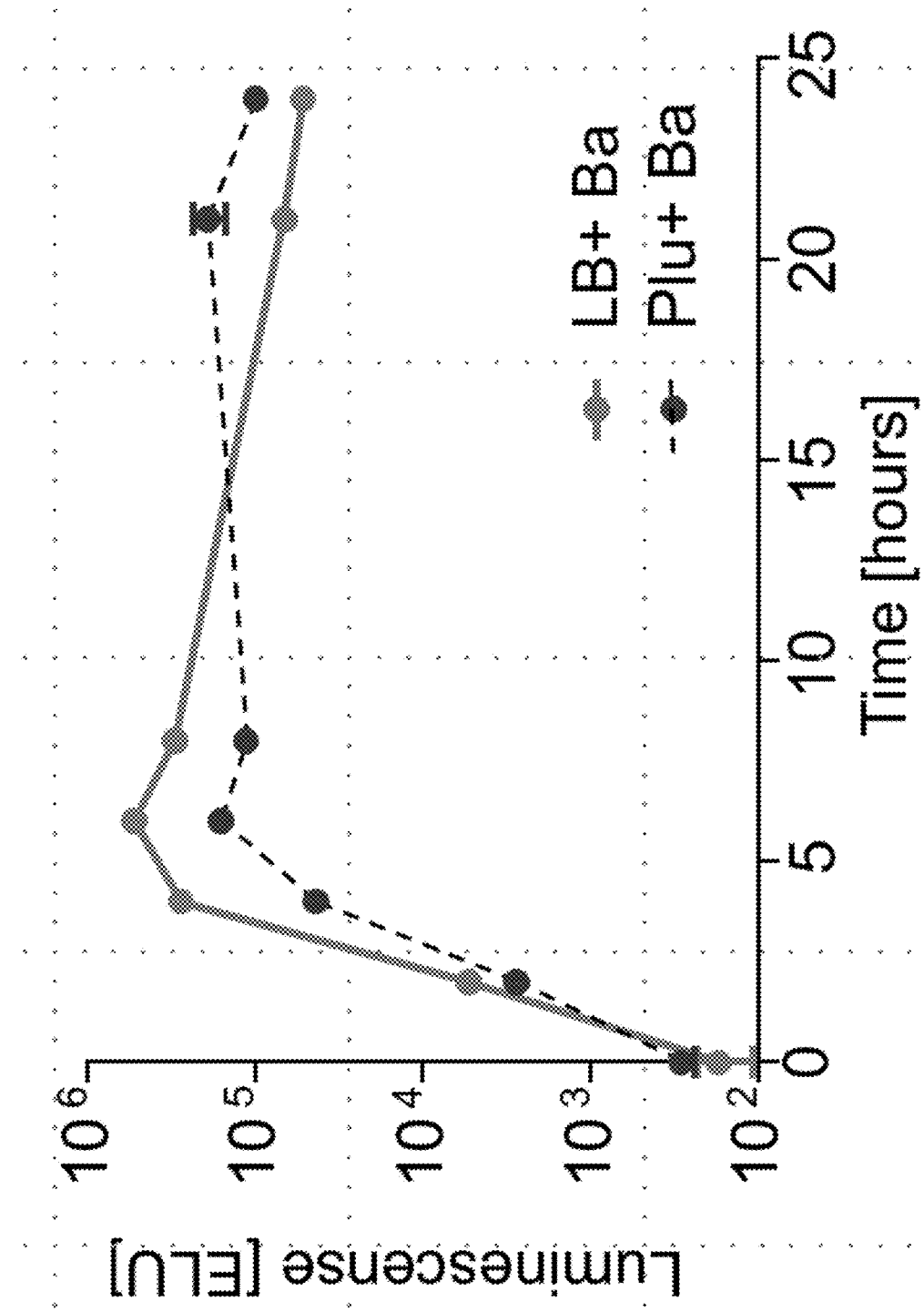

FIG. 3 presents luminescence measurements over time for LB+bacteria (Ba) and Pluronic, (Plu)+Ba.

Figure 4A:
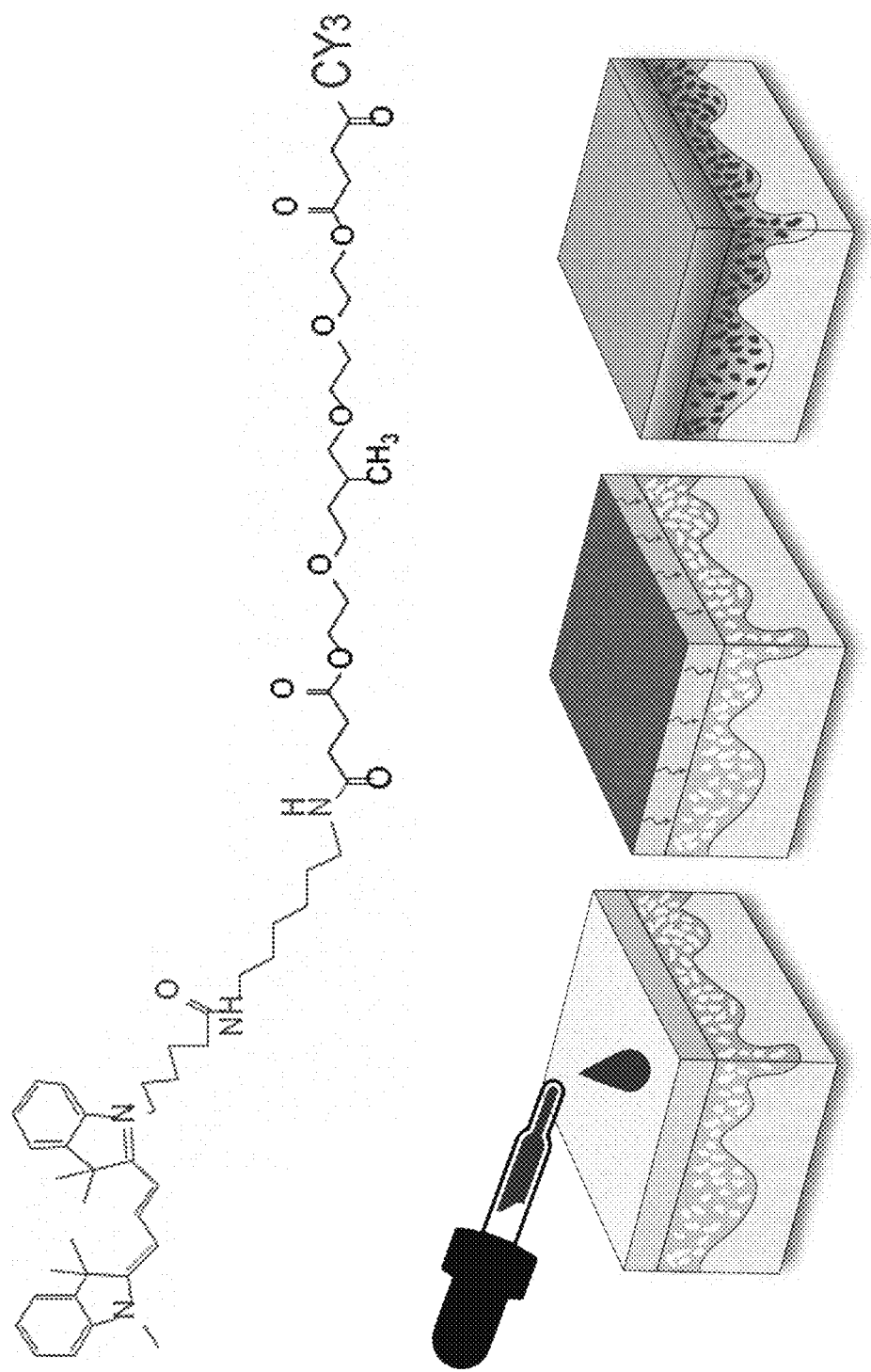
Figure 4B:
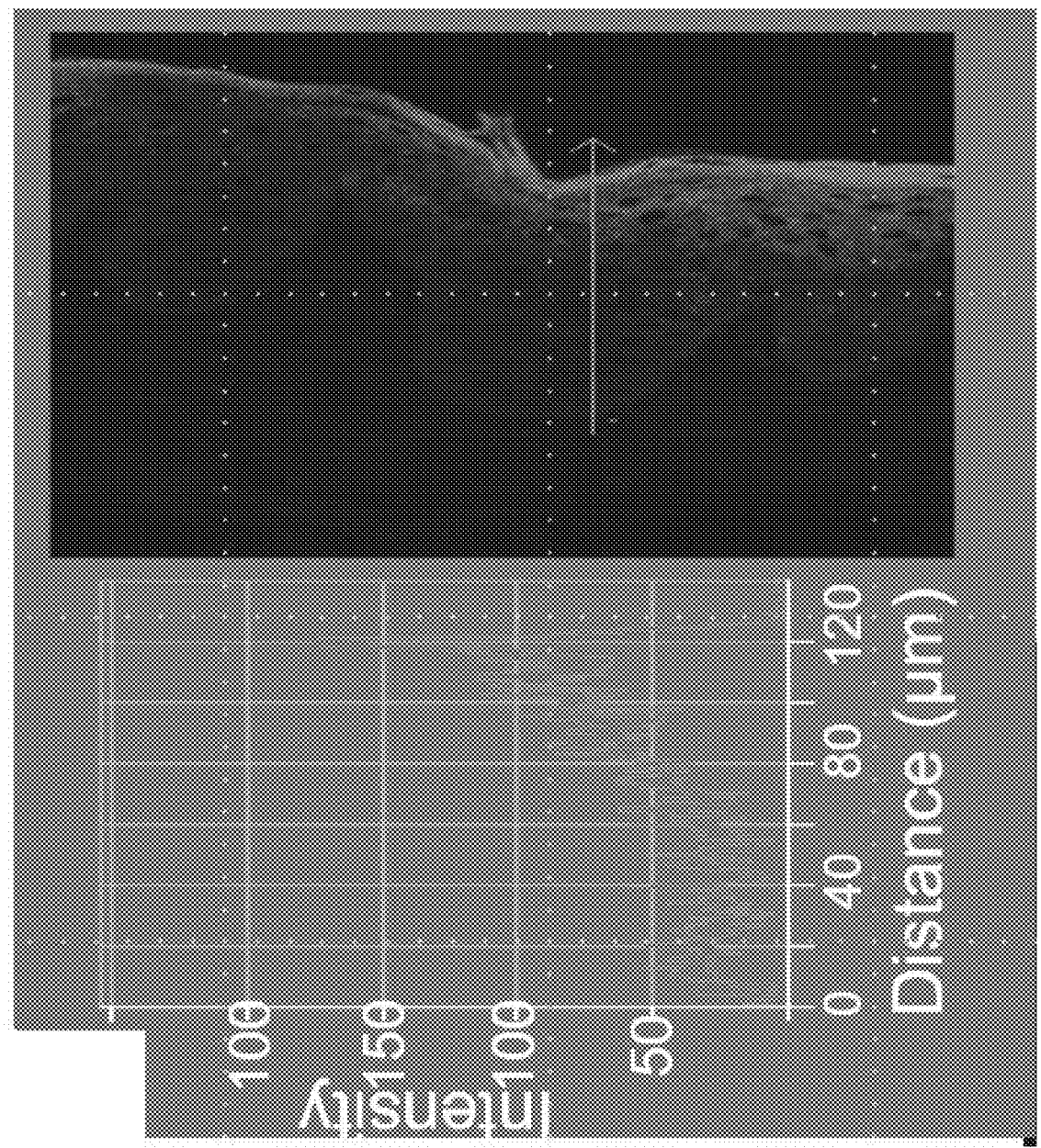

FIGS. 4A-F present a penetration experiment: Pluronic substitution with cyanine 3 amine cy3 (FIG. 4A). Formulation skin depth analysis under microscope, the formula penetrated via the stratum corneum and accumulated in the epidermis (FIG. 4B). Skin histology cuts under confocal microscopy in brightfield (FIG. 4C), GFP (Green fluorescent protein; FIG. 4D), Ch3 (FIG. 4E), and merge (FIG. 4F), respectively.

Figure 5:
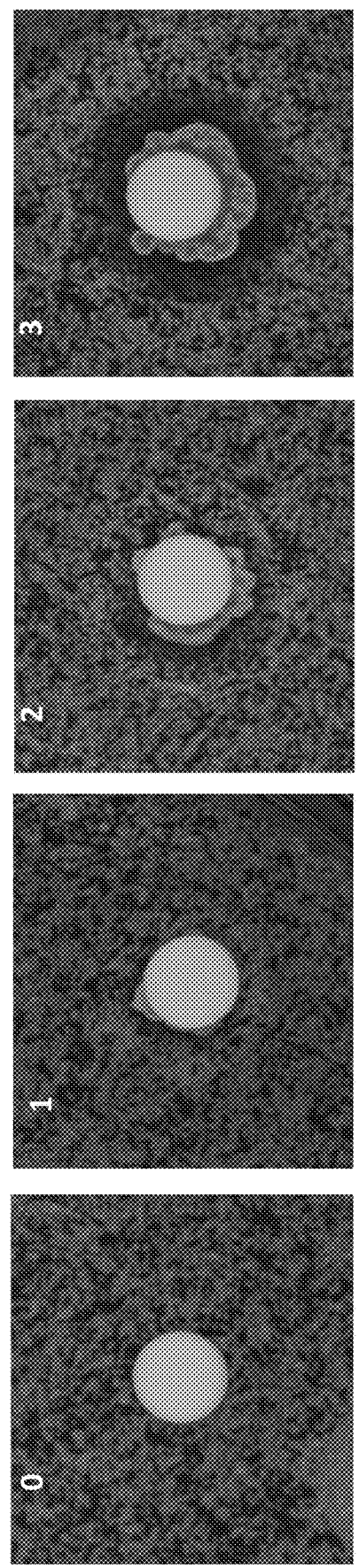

FIGS. 5 presents indexes 1 to 3 for Table 1 for inhibition activity of different types of Bacillus on two types of *Candida*.

Figure 6A:
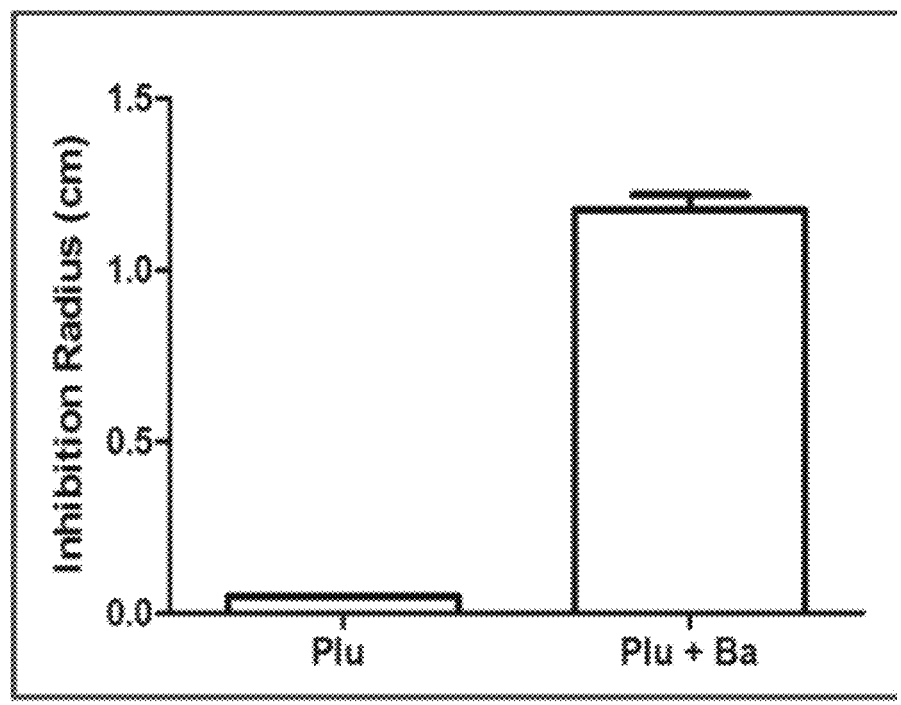
Figure 6B:
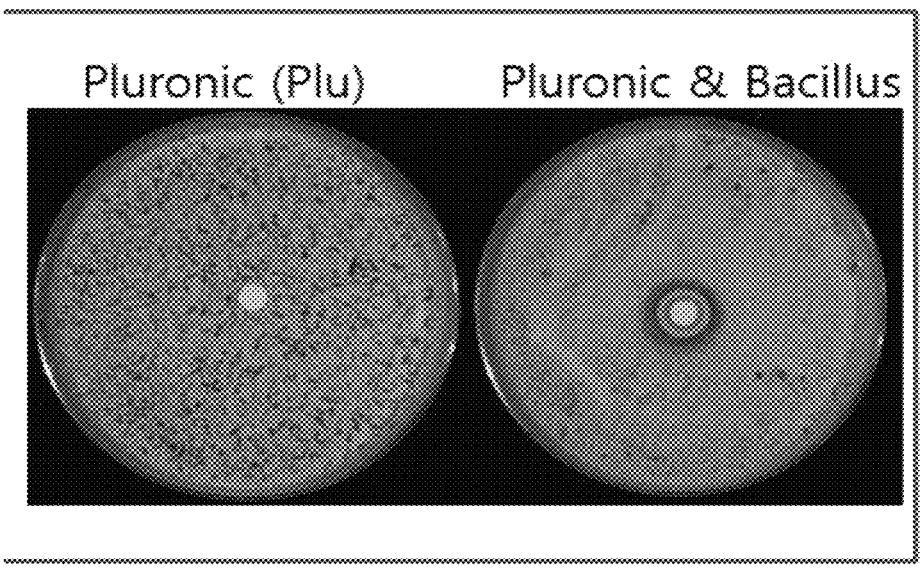

FIGS. 6A-B present Candida Albicans diploid inhibition with *Bacillus subtilis* 3610. Inhibition radius measurements (FIG. 6A). Inhibition areas on agar plates (FIG. 6B).

Figure 7:
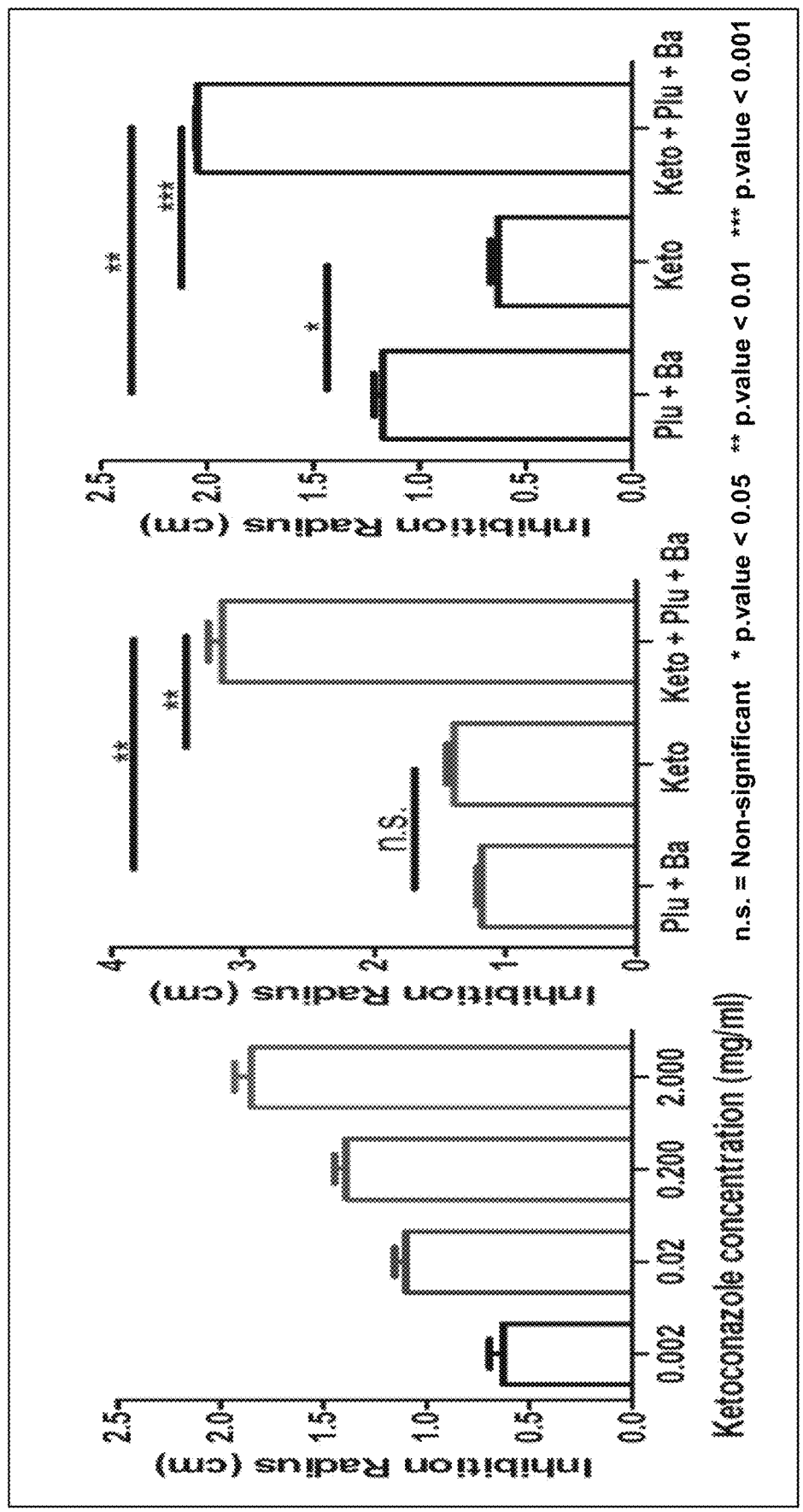

FIG. 7 presents Candida Albicans diploid inhibition with *Bacillus subtilis* 3610 and ketoconazole.

Figure 8A:
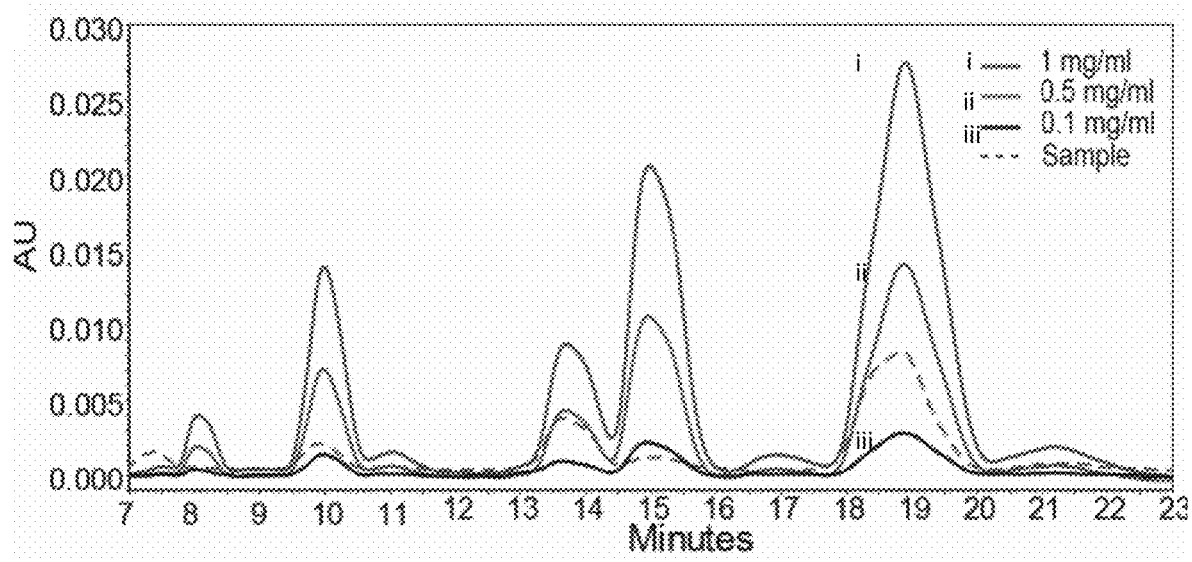
Figure 8B:
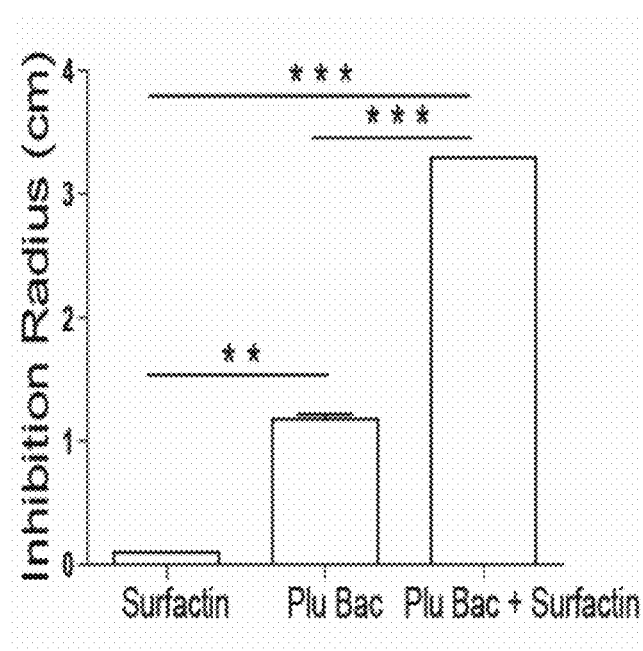

FIGS. 8A-B present Surfactin analysis. HPLC results—Surfactin extract (FIG. 8A), and Candida Albicans diploid inhibition with *Bacillus subtilis* 3610 and Surfactin (FIG. 8B).

Figure 9A:
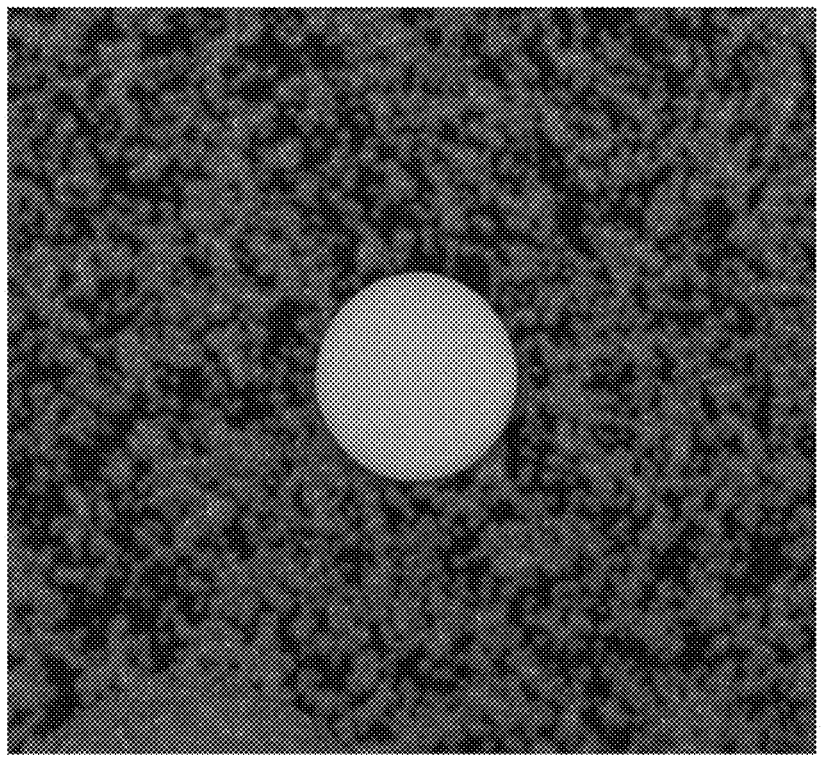
Figure 9B:
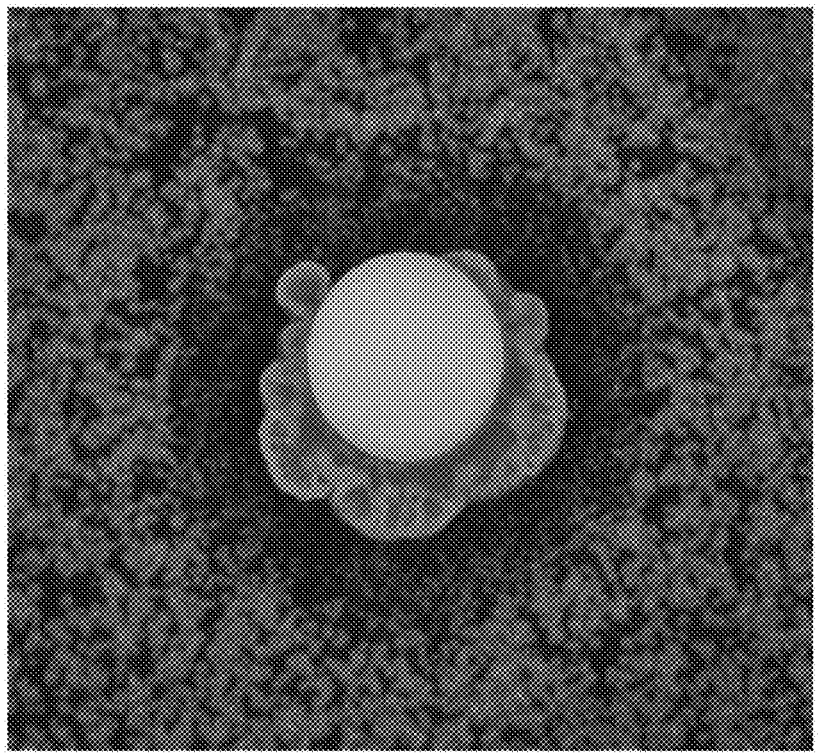

FIGS. 9A-B present Candida Albicans inhibition by *Bacillus subtilis* 3610 after 48 hours; Control (pure LB medium) (FIG. 9A) and $10^7$ *Bacillus subtilis* in LB medium (FIG. 9B).

Figure 10A:
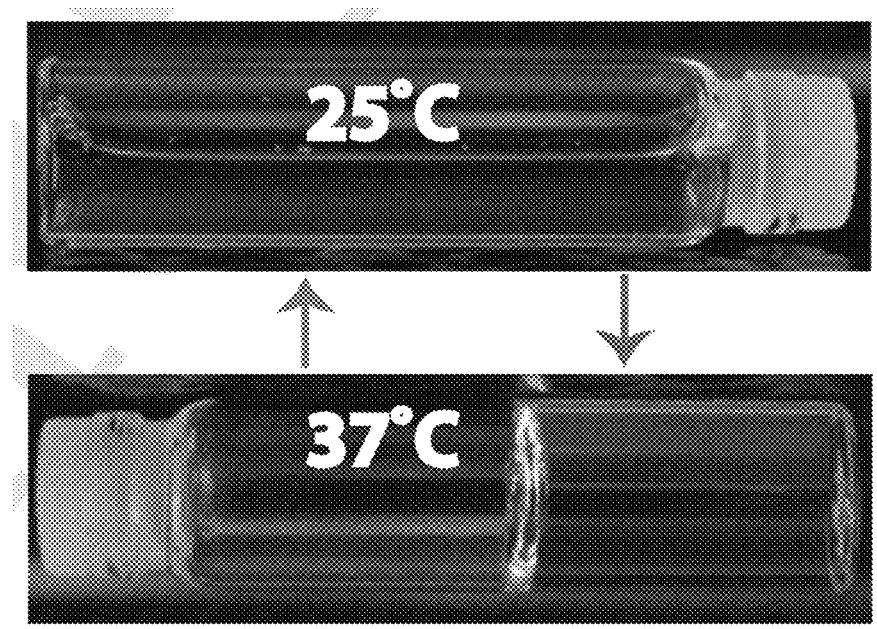
Figure 10B:
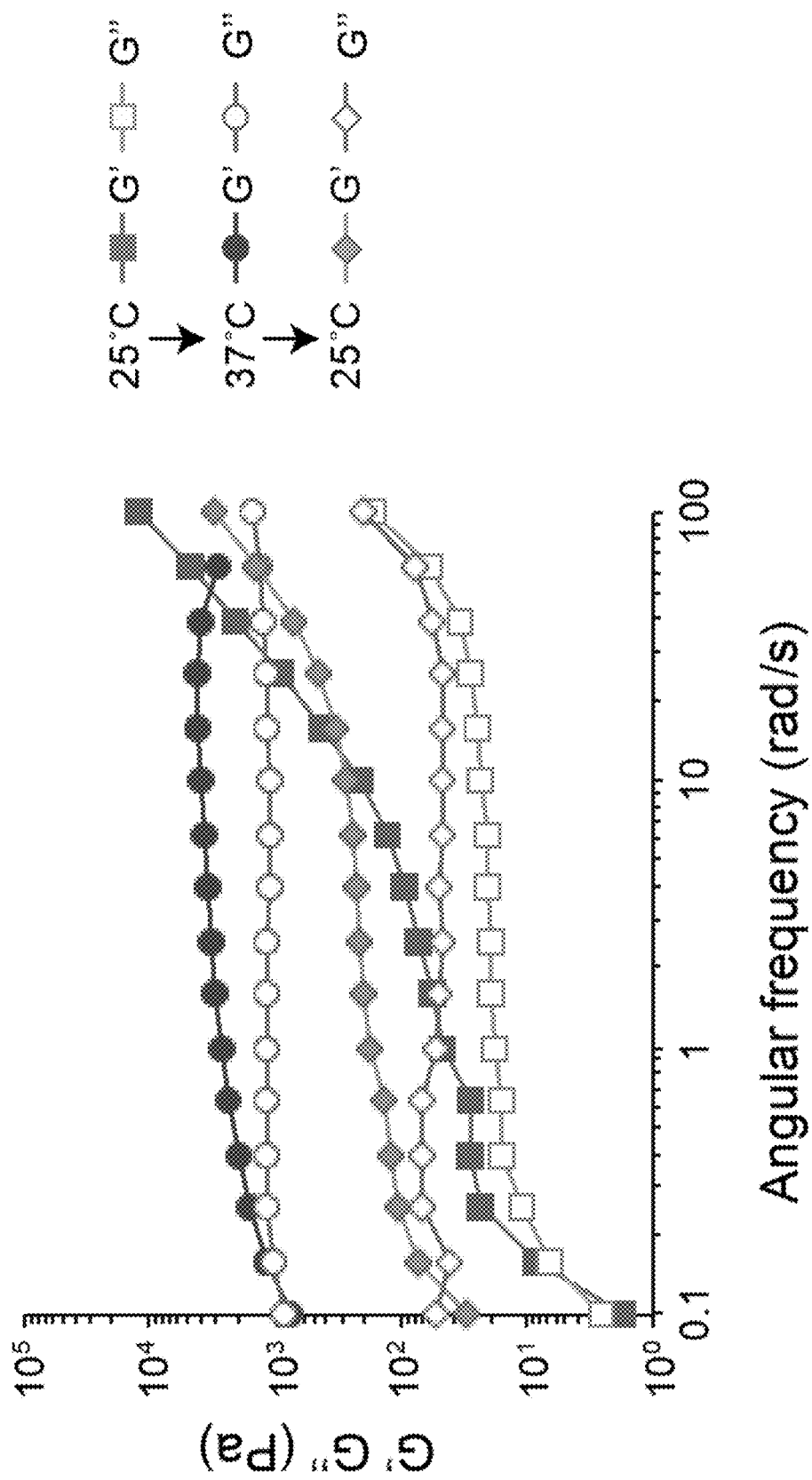

FIGS. 10A-B present a gelation properties and characterization: reversible transformation of pluronic solution (18% w/v) from liquid at 25° C. to gel at 37° C. (FIG. 10A), and storage and loss moduli (G', G") as a function of angular frequency of pluronic+LB+*Bacillus subtilis* (10:1) (1% strain) in temperature changes from 25° C. to 37 ° C. and back to 25° C. (FIG. 10B).

Figure 11:
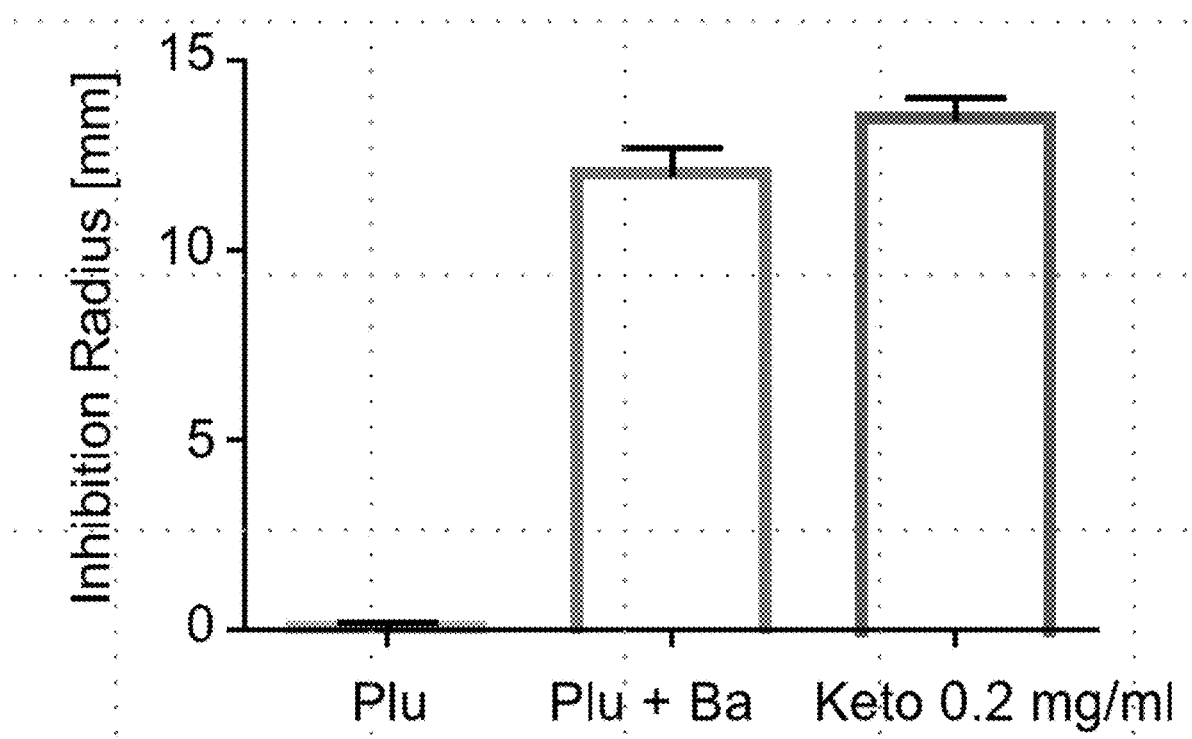

FIG. 11 presents antifungal activity of pluronic (Plu), *bacillus* formula (Plu+Ba) and ketoconazole (Keto 0.2 mg/ml) against *C. albicans*.

FIGS. 12A-B present the general structure of Surfactin (FIG. 12A) and total ion chromatogram of surfactin (FIG. 12B) extracted from *B. subtillis* cultivated in the thermo-responsive formula (90% pluronic/10% LB).

Figure 13:
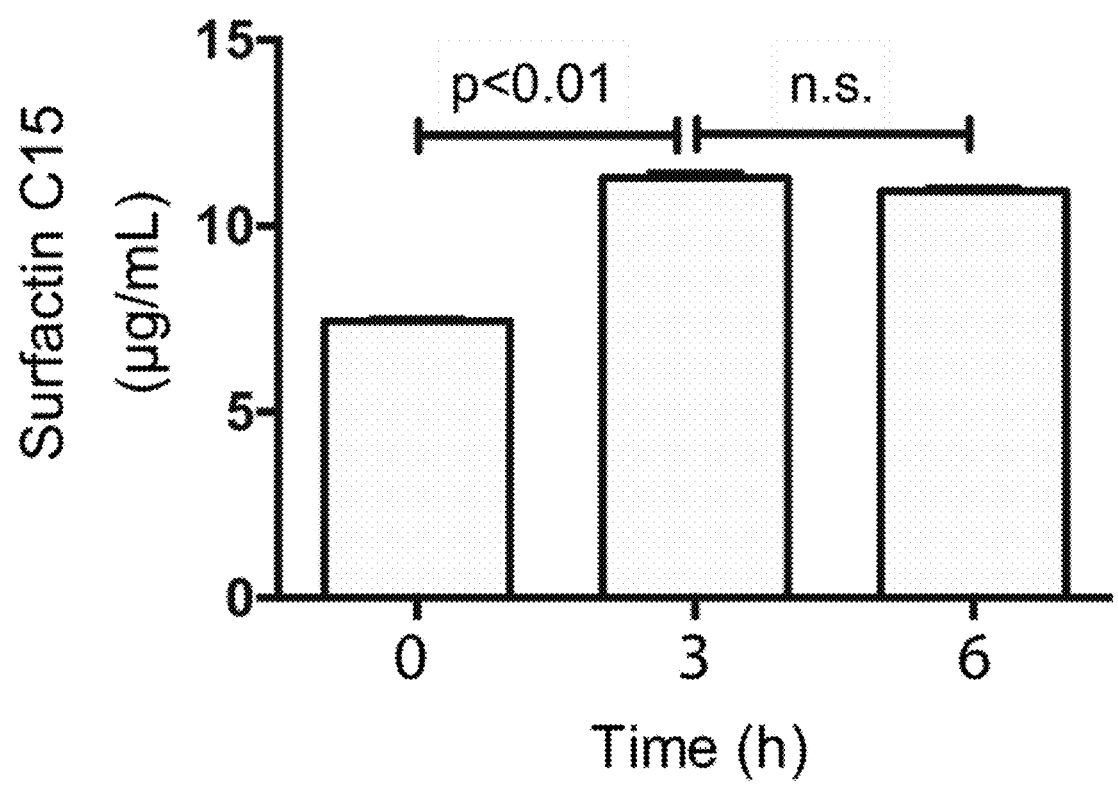

FIG. 13 presents Surfactin C15 production over time from *B. subtillis* cultivated in the thermo-responsive formula (90% pluronic/10% LB).

Figure 14:
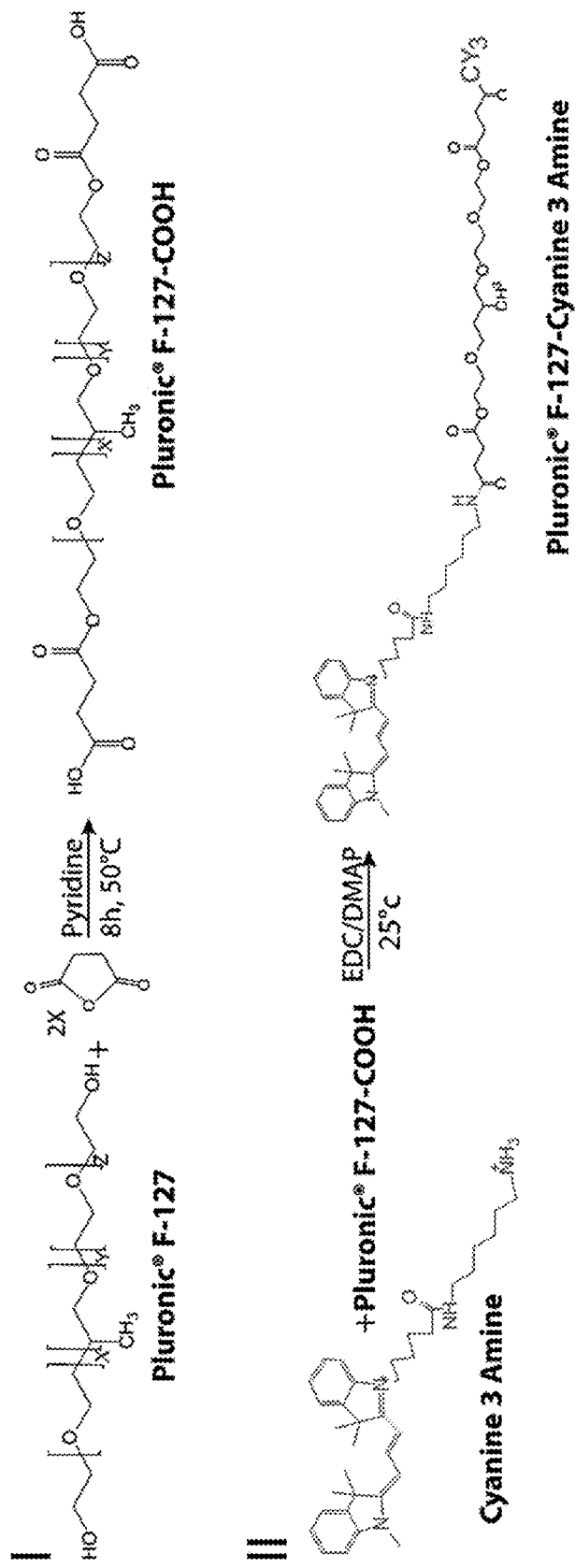

FIG. 14 presents the synthetic steps to reach Pluronic® F-127-cyanine 3.

FIGS. 15A-J present histology of skin tissue 4 and 10 days after injection of C. albicans to the dorsal region and daily treatment. Hematoxylin and eosin staining of skin (FIGS. 15A-H) Histological scores for inflammation (FIGS. 15I-J) (data expressed as means±SD; n=6 per group) were compared by a one-way ANOVA with Tukey post hoc comparison (*P<0.05). Arrows indicate areas of inflammation. Photographs are representative views.

DETAILED DESCRIPTION OF THE INVENTION

The present invention provides kits and compositions comprising living bacteria incorporated in a thermo-responsive hydrogel characterized by a viscosity suitable for hardening after administration on a subject's skin, wherein the bacteria continuously produces and secretes therapeutic or cosmeceutical agents. The present invention further provides methods for topically delivering a therapeutic or cosmeceutical agent such as for inhibiting or reducing growth of microorganisms on a subject's skin.

According to one aspect, there is provided a kit comprising:

(i) a material (also referred to as "matrix") characterized by a viscosity that is less than about 1 Pa, or, in some embodiments, less than 5 Pa or, in some embodiments, less than 10 Pa under a first stimulus, and a viscosity that is higher than about 30, 40, 50, 60, 70, 80, 90, 100, 200, 300, 400, 500, or higher than 1000 Pa, under a second stimulus; and one or more from: (ii) a bacterial growth medium, and (iii) bacteria.

In some embodiments, there is provided a composition or a formulation comprising:
(i) a material (also referred to as "matrix") characterized by a viscosity that is less than about 1 Pa, or, in some embodiments, less than 5 Pa or, in some embodiments, less than 10 Pa under a first stimulus, and a viscosity that is higher than about 30, 40, 50, 60, 70, 80, 90, 100, 200, 300, 400, 500, or higher than1000 Pa, under a second stimulus;
(ii) a bacterial growth medium, and
(iii) bacteria.

In some embodiments, the composition is constructed from material which is responsive to one or more preselected stimulus and which change their physical state in response to such a stimulus.

In some embodiments, the material is tailored to display substantial property changes, in response to stimuli. The "stimulus" may be mechanical stress, chemical, physical or biological stimuli, e.g., temperature (including external heat radiation and internal heat formation), pH, ionic strength, biochemical agents, or application of magnetic or electrical fields. In some embodiments, the stimulus is applied continuously; for example, the composition is maintained at a certain temperature. In further embodiments, the stimulus is transient or is applied over a period of time sufficient to transform all or a portion of the material or composite into the desired physical state.

In some embodiments, the stimulus is a mechanical stress (e.g., static, quasi-static or dynamic). In some embodiments, the stimulus is heat generated due to another stimulus (such as the heat generated due to mechanical impact).

In exemplary embodiments, the stimulus is temperature. In some embodiments, the stimulus is heat generated due to another stimulus (such as the heat generated due to mechanical impact).

In some embodiments, the viscosity of the second physical state is higher than the viscosity of the first physical state.

In some embodiments, the viscosity of the second physical state is 2 times, 5 times, 10 times the viscosity of the first physical state, or is 14, 15, 16, 18, 20, 22, 24, 26, 28, 30, 32, 33, 34, 35, 36, 37, 38, 40, 50, 60, 70, 80, 90, or 100 times the viscosity of the first physical state.

The terms "bacterial growth medium", "growth medium" and "growth culture" are intended to mean a medium used for the growth of bacteria in a culture comprising components necessary for growth of the bacteria, such as a carbon/energy source.

In some embodiments, the growth medium is selected from, but is not limited to, gel, agar, and broth.

One skilled in the art would also recognize that various growth media can be employed, for example, Luria Broth (LB), NZCYM Broth, Brain-Heart-Infusion (BHI), Minimal-Media-Davis (MMD), Mann-Rogosa-Sharpe broth (MRS) or simple chemical media. There may also be added to the medium, a substance for inducing the growth of a bacterium. Either complex or chemical media may be used to grow the bacteria.

In some embodiments, the nutrient medium for the growth of bacteria contains sources of assimilable carbon and nitrogen, as well as mineral salts. Suitable sources of assimilable carbon and nitrogen include, but are not limited to, complex mixtures, such as those constituted by biological products of diverse origin, for example soy bean flour, cotton seed flour, lentil flour, pea flour, soluble and insoluble vegetable proteins, corn steep liquor, yeast extract, yeast and casein hydrolysates, peptones and meat extracts.

In some embodiments, any sources may be used for the nitrogen source of the medium as long as the bacteria can utilize them. Additional sources of nitrogen include simple, synthesizable organic and inorganic compounds such as ammonium salts, alkali nitrates, amino acids, nitrates, such as ammonium chloride, ammonium sulfate, sodium nitrate and potassium nitrate.

In some embodiments, any sources may be used for the carbon source of the medium as long as the bacteria can utilize them. Specifically, there may be used sugars such as glucose, fructose, sucrose, maltose, mannose, glycerin, millet jelly, molasses, dextrin, starch, and sorbitol; alcohols such as methanol, ethanol, and glycerol; organic acids such as fumaric acid, citric acid, acetic acid, and propionic acid and their salts; hydrocarbons such as paraffin; and mixtures of the foregoing. Nutrition sources may also be added appropriately to the medium, which are used in culturing, including inorganic salts, the salts of minute metals, and vitamins. Generally, the nutrient medium may include, but is not limited to, the following ions: $Mg^{++}$, $Na^+$, $K^+$, $Ca^{++}$, $NH_4^+$, $Cl^-$, $SO_4^-$, $PO_4^-$ and $NO_3^-$, and also ions of the trace elements such as Cu, Fe, Mn, Mo, Zn, Co and Ni. The preferred source of these ions is mineral salts.

In some embodiments, by "bacteria" it is meant to refer to bacterial cells of bacteria such as, for example, Gram-positive and Gram-negative bacteria. In some embodiments, by "bacteria" it is meant to refer to viable bacterial cells. In some embodiments, by "bacteria" it is meant to refer to a population of viable bacteria.

In some embodiments, by "population of viable bacteria" it is meant to refer to the lag phase of the bacterial population growth. In some embodiments, by "population of viable bacteria" it is meant to refer to the log phase of the bacterial population growth. In some embodiments, by "population of viable bacteria" it is meant to refer to the stationary phase of the bacterial population growth.

In some embodiments, the composition comprises bacteria at a concentration in the range of $10^5$ to $10^{15}$ CFU (colony-forming units). In some embodiments, the composition comprises bacteria at a concentration in the range of $10^5$ to $10^{10}$ CFU, $10^5$ to $10^9$ CFU, $10^6$ to $10^9$ CFU, or $10^7$ to $10^9$ CFU, including any range therebetween. In some embodiments, by population of bacteria it is meant to refer to bacteria are at a concentration of $10^7$-$10^9$ CFU/ml.

In some embodiments, by "bacteria" it is meant to refer to non-pathogenic bacteria. The term "non-pathogenic bacteria" means bacterial strains incapable of causing disease in an animal (e.g., mammal) under normal conditions.

In some embodiments the bacteria are probiotic bacteria.

In some embodiments, the non-pathogenic bacteria are GRAS bacteria. The term "GRAS" comes from the acronym of "Generally Recognized as Safe". This designation GRAS is the work of the FDA (American Food and Drug Administration) and means that the addition of the chemical or substance that is concerned, it is considered safe by experts of the organization.

Non-limiting examples of genus of non-pathogenic bacteria are selected from: *Exempleri Acinetobacter, Actinomycetales, Anaerococcus, Bacillales, Bifidobacterium, Enhydrobacter, Enterococcus, Finegoldia, Carnobacterium, Coryneobacterium, Lactobacillus, Lactococcus, Leunconostoc, Macrooccus, Micrococcineae, Oenococcus, Pediococcus, Peptomphilus, Propionibacterium, Salinicoccus, Sphingomonas, Strepococcus, Tetragenoccus*, and *Weissella*.

In some embodiments, the bacteria are selected from, without being limited thereto, *Bacillus subtilis, Bacillus uniflagellatus, Bacillus lateropsorus, Bacillus laterosporus* BOD, *Bacillus megaterium, Bacillus polymyxa, Bacillus lichenifonnis, Bacillus pumilus, Bacillus sterothermophilus, Lactobacillus casei, Lactobacillus reuteri, Lactobacillus acidophilus, Lactobacillus jensenii, Bifidobacterium lognum, Bifidobacterium reuteri, Bifidobacterium lactis, Bifidobacterium breve, Bifidobacterium animalis, Propionibacterium acidipropionici, Propionibacterium freudenreichii, Propionibacterium thoenii,* and *Propionibacterium jensenii*.

In some embodiments, the bacteria are naturally found onto a human skin or a mucus.

Herein, by "bacteria" it is also meant to encompass dormant or spores of the selected bacterial cells.

In some embodiments, the bacteria are capable of producing one or more agents (e.g., peptides) exhibiting a biologically therapeutic effect. In some embodiments, the term "peptide" means a polymer comprising amino acids linked via peptide bonds. A peptide according to the invention may comprise two or more amino acids, for example, 2, 3, 4, 5, 6, 7, 8, 9, 10, 15, 20, or more.

The term "therapeutic effect" refers to the reduction, elimination, and/or prevention of a disease, symptoms of the disease, or side effects of a disease in a subject.

In some embodiments, the term "therapeutic effect" refers to an activity against a microorganism (e.g., prokaryotes, archaea, bacteria, eukaryotes, protists, fungi, algae, euglena, protozoan, dinoflagellates, apicomplexa, trypanosomes, viruses, amoebae and the likes).

In some embodiments, the term "therapeutic effect" refers to antifungal activity (or effect).

Further embodiments of the therapeutic effect are described hereinbelow under "The method of treatment".

In exemplary embodiments, the bacteria is *Bacillus Subtilis*. In exemplary embodiments, the bacteria exhibit antifungal activity.

In some embodiments, the term "antifungal activity" includes preventing, inhibiting the growth of a fungus (e.g., fungistatic activity), killing at least a portion of the fungus (e.g., fungicidal activity), limiting the ability of the fungus to reproduce, etc.

In some embodiments, the term "inhibiting the growth of a fungus" includes both fungistatic and fungicidal activity. Fungistatic activity includes any decrease in the rate of growth of a fungal colony. Fungistatic activity may be manifested by a fungus maintaining its present size or failing to colonize the surrounding areas. Fungistatic activity may be a result of inhibition of the fungal reproductive processes. Fungicidal activity generally includes, for example, irraditication of a fungus or fungal colony, killing a fungus or fungal colony or, in one embodiment, a decrease in the mass or size of a fungus or fungal colony.

In some embodiments, the term "preventing" in the context of microorganism, e.g., antifungal activity, indicates that the growth rate of the fungal cells is essentially nullified or is reduced by at least 20%, at least 30%, at least 40%, at least 50%, at least 60%, at least 70%, at least 80%, or at least 90% of the appearance of the fungal cells in a comparable situation lacking the presence of the bacteria or a composition containing the produced peptides.

Alternatively, preventing means a reduction to at least 15%, 10% or 5% of the appearance of the fungal cells in a comparable situation lacking the presence of the bacteria or a composition containing the produced peptides. Methods for determining a level of appearance of fungal cells are known in the art.

In some embodiments, the kit is for use for dermatological infection e.g., dermatological fungal infection.

In some embodiments, dermatological fungal infection is selected from, but is not limited to, a skin mycosis including any disorders, symptoms or conditions associated thereof, tinea pedis, tinea corporis, tinea cruris, jock itch, tinea and ringworm.

Further embodiments of the use of kit are described hereinbelow under "The method of treatment".

In some embodiments, the concentration of the matrix is adjusted to render the composition with a desired liquid-gel transition.

In some embodiments, the concentration (w/v) of the growth medium within the disclosed composition is 60% to 90%. In some embodiments, the concentration (w/v) of the growth medium within the disclosed composition is 70% to 85%. In some embodiments, the concentration (w/v) of the growth medium within the disclosed composition is 75% to 85%. In some embodiments, the concentration (w/v) of the growth medium within the disclosed composition is 80% to 90%. In some embodiments, the concentration (w/v) of the growth medium within the disclosed composition is 80% to 85%.

In some embodiments, the concentration (w/v) of the growth medium within the disclosed composition is selected so as to exhibit gelation after time duration of 20 sec to 15 min, or from 30 sec to 10 min, upon contacting with a skin or a mucus membrane of a subject (e.g., as further detailed under "the method of treatment").

In some embodiments, the amount of the matrix within the disclosed composition is in the range of from 10% (w/v) to 30% (w/v). In some embodiments, the amount of the matrix is within the disclosed composition in the range of from 12% (w/v) to 30% (w/v), 13% (w/v) to 30% (w/v), 14% (w/v) to 30% (w/v), 10% (w/v) to 20% (w/v), 13% (w/v) to 20% (w/v), or 14% (w/v) to 20% (w/v), including any range therebetween.

In some embodiments, the ratio of the matrix and the growth medium is in the range from 1:1 (v/v) to 20:1(v/v).

In some embodiments, the ratio of the matrix and the growth medium is in the range from 2:1 (v/v) to 20:1(v/v), 5:1 (v/v) to 20:1(v/v), 5:1 (v/v) to 15:1(v/v), 8:1 (v/v) to 20:1(v/v), 9:1 (v/v) to 20:1(v/v), or 9:1 (v/v) to 15:1(v/v), including any range therebetween.

In some embodiments, the matrix is a revere thermo-responsive compound (e.g., in the form of a gel). In some embodiments, the compound is a polymeric compound (also referred to as "polymer").

In some embodiments, the term "polymer", as used here-inthroughout, describes a substance, composed of a plurality of repeating structural units (referred to interchangeably as backbone units or monomeric units), e.g., being covalently connected to one another and forming the polymeric backbone of the polymer. The term "polymer" as used herein encompasses organic and inorganic polymers and further encompasses one or more of a homopolymer, a copolymer or a mixture thereof (e.g., a blend).

In some embodiments, the term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

As used herein, the terms "revere thermo-responsive material", "reverse-freezing material" (interchangeably "thermo-sensitive", "thermo-responsive", "thermo-gelating", "thermo-solidifying" and/or including the prefix "reverse" to any of these materials) refers to a substance that is characterized by undergoing full or partial: solidification, crystallization, gelation, phase-separation or increase their viscosity without any apparent loss of solvent, upon heating and/or increasing temperature. In some embodiments, the reverse-freezing material undergoes at least partial solidification, gelation or crystallization upon heating.

In some embodiments, the thermo-sensitive gels employed in accordance with the invention is classified as a gel having lower critical solution temperatures (LCST).

In some embodiments, the water or the growth medium solutions of these materials display low viscosities at low temperatures (below, at or above ambient temperature), and exhibit a sharp viscosity increase as the temperature rises within a very narrow temperature interval, producing a semi-solid gel once they reach the body temperature. In the case of the present invention, the thermal transition has to be below the temperature of the skin or the mucus.

In some embodiments, the matrix is classified GRAS, as defined hereinabove.

In some embodiments, the thermo-responsive materials are polymers such as poly(ethylene oxide)-poly(propylene oxide)-poly(ethylene oxide) (PEO-PPO-PEO) triblocks, random or alternating reverse thermo-responsive PEO-PPO block copolymers, tetrafunctional block polymers of polyoxyethylene and polyoxypropylene condensed with ethylenediamine, N-alkyl substituted acrylamides (preferably poly-N-isopropyl acrylamide [PNIPAAm], cellulose derivatives, selected from hydroxypropyl methylcellulose and hydroxypropyl cellulose, alternating or random, and various amphiphilic polymers such as poly(ethylene oxide)-polylactic acid block copolymers, and combinations thereof. In some embodiments, the polymers used in accordance with the present invention are selected to have a thermal transition within the physiologically relevant temperature range, relevant to a skin or a mucus of a body.

In other embodiments, the composition comprises at least one polymer selected amongst polymers belonging to the family of poly(ethylene oxide)/poly(propylene oxide)/poly(ethylene oxide) (PEO-PPO-PEO) triblocks, commercially available as Pluronic, or a derivative thereof.

In exemplary embodiments, the composition comprises $\{EO\}99\text{-}\{PO\}67\text{-}\{EO\}99$ triblock, known as Pluronic F127, or its carboxylated form. In exemplary embodiments, the polymer is functionalized e.g., by a dye group. Further embodiments are described in the Examples section below.

In some embodiments, based on the selection of matrix, the composition may be deployed onto a skin or mucus below their thermal transition, where they exhibit low viscosity, making a topical administration of them onto the skin or the mucus easy and simple. Upon contact with the skin or the mucus, due to their higher temperature, at typically 34-36° C., the low viscosity solution suitably gels, to generate a stable shield on the skin. Due to the versatility of the polymers utilized in the composition of this invention, the gels formed may be tailored and fine-tuned over a broad range of rheological and mechanical properties.

In some embodiments, the first stimulus is a temperature below 35° C., or, in some embodiments, below 30° C. and the second stimulus is a temperature above 35° C.

In some embodiments, the matrix is capable of penetrating up to the epidermal skin layer. In some embodiments, the matrix is capable of penetrating the epidermal skin layer while avoiding contact with the nerves below the epidermal skin layer. In some embodiments, the matrix is capable of penetrating the epidermal skin layer while avoiding contact with the blood vessel below the epidermal skin layer.

As exemplified in the Examples section below, the growth medium and/or the bacteria are at a concentration that substantially (e.g., less than ±10%) does not affect the rheological property of the matrix at a defined temperature.

For example, as exemplified in the Examples section below, the storage modulus G' can be measured as a function of temperature. For example, G' as a function of temperature can be measured using a temperature ramp at a fixed frequency and strain in a rheometer.

In some embodiments, the phrase "storage modulus" refers to a measure of elastic response of a material. In some embodiments, the phrase "loss modulus" refers to a measure of the viscous property of a fluid.

In some embodiments, the value G' is substantially stable at a specified temperature and independent of the growth medium and bacteria e.g., up to 90% w/v of the growth medium.

In some embodiments, the bacteria form a biofilm in/on the matrix.

In some embodiments, the term "biofilm", as used herein, refers to an aggregate of living cells which are stuck to each other and/or immobilized onto a surface as colonies. The cells are frequently embedded within a self-secreted matrix of extracellular polymeric substance (EPS), also referred to as "slime", which is a polymeric sticky mixture of nucleic acids, proteins and polysaccharides.

Method of Treatment

In some embodiments, there is provided a method for topically delivering a therapeutic or cosmeceutical agent to by topically applying to a subject the disclosed composition.

In some embodiments, there is provided a method of treating or preventing disease or disorder on a mucus or a skin by topically applying thereon the disclosed composition.

In some embodiments, by "mucus" it is meant to refer to mucus membrane.

In some embodiments, there is provided a method of inhibiting or reducing the formation of load of fungi on mucus or a skin, the method comprising contacting the disclosed composition comprising the bacteria with an outer layer region of the mucus or the skin. In some embodiments, the method is applied by a topical treatment of dermatological infections.

In some embodiments, the inhibition or the reduction of the formation of load of microorganism (e.g., fungi) on a mucus or on a skin is affected for at least 0.5 h, at least 1 h, at least 2 h, or at least 3 h, upon applying the disclosed composition outer layer region of the mucus or the skin.

In some embodiments, the method is for the treatment of fungal dermatological infection. In exemplary embodiments, the fungal dermatological infection is caused by *Candida albicans*.

Thus, a method utilizing the disclosed composition according to the invention may comprise topically administering the composition onto the skin or onto the mucus at a first physical state (i.e. lower viscosity) measured under a stimulus outside the skin or the mucus; and affecting a second stimulus while the disclosed composition is on the skin is to transition to a second desirable physical state (i.e. higher viscosity). In some cases, the transition to the second physical state may be spontaneous upon contacting the mucus or the skin.

In some embodiments, by "spontaneous", it is meant e.g., within 30 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, or within 30 min, including any value and range therebetween.

In some embodiments, fungal infections which may be treated are selected from, but are not limited to, aspergillosis, cryptococcosis, North American blastomycosis, invasive and systemic candidiasis, coccidioidomycosis, paracoccidioidomycosis, histoplasmosis, fusariosis, invasive trichosporonosis, phaeohyphomycosis, sporotrichosis, zygomycosis (mucormycosis) due to susceptible species of these genera.

In some embodiments, the dermatological fungal infection is a mild to moderate infection. In other embodiments, the dermatological fungal infection is a moderate to severe infection.

It should be understood that the terms "moderate topical fungal infection symptoms" or "moderate to severe topical fungal infection symptoms" relate to the intensity of the dermatological symptoms shown on the skin of the subject at the infection site which include at least one of erythema, scaling, maceration, burning and pruritus or any combinations thereof. Such intensity of infectious symptoms are determined by a medical practitioner.

Kits

In some embodiments, the term "kit", as used herein, refers to a single package containing any collection of items or components needed for a specific purpose, especially for use by a user or an operator. In some embodiments, the kit is in a form wherein some of the ingredients of any one of the components (i)-(iii) presented herein, are packaged individually (separately) within the kit. In some embodiments, the kit may include one or more of the compositions in a ready-for-use form, packaged together within the kit.

In some embodiments, the kit comprises the at least one (i) matrix, (ii) a bacterial growth medium, and (iii) bacteria packaged within a container.

In some embodiments, the container is made of a material selected from the group consisting of thin-walled film or plastic (transparent or opaque), paperboard-based, foil, rigid plastic, metal (e.g., aluminum), glass, etc.

In some embodiments, the content of the kit is packaged, as described below, to allow for storage of the components until they are needed.

In some embodiments, some or all components of the kit may be packaged in suitable packaging to maintain sterility.

In some embodiments of the subject kits, the matrix, bacterial growth medium, and bacteria are stored in separate containers within the main kit containment element e.g., box or analogous structure, may or may not be an airtight container, e.g., to further preserve the sterility of some or all of the components of the kit.

In some embodiments, the dosage amount of the one or more matrix, one or more bacterial growth medium, and one or more bacteria and provided in a kit may be sufficient for a single application or for multiple applications.

In those embodiments, the kit may have multiple dosage amounts of the one or more matrix, one or more bacterial growth medium, and one or more bacteria packaged in a single container, e.g., a single tube, bottle, vial, Eppendorf and the like.

In some embodiments, the kit may have multiple dosage amounts of the one or more matrix, one or more bacterial growth medium, and one or more bacteria individually packaged such that certain kits may have more than one container of one or more matrix, one or more bacterial growth medium, and one or more bacteria.

In some embodiments, multiple dosage amounts of the one or more matrix, one or more bacterial growth medium, and one or more bacteria may be packed in single separate containers.

In some embodiments, the kit comprises instructions for topical application onto a mucus or skin of the subject.

In some embodiments, the kit comprises instructions for mixing a matrix and growth medium at a ratio ranging from 1:1 (v/v) to 20:1(v/v). the kit comprises instructions for mixing a matrix and growth medium at a ratio ranging from 2:1 (v/v) to 20:1(v/v), 5:1 (v/v) to 20:1(v/v), 5:1 (v/v) to 15:1(v/v), 8:1 (v/v) to 20:1(v/v), 9:1 (v/v) to 20:1(v/v), or 9:1 (v/v) to 15:1(v/v), including any range therebetween.

In some embodiments, the kit contains instructions for preparing a composition as described elsewhere herein, and for practicing the methods of the invention.

In some embodiments, the instructions may be recorded on a suitable recording medium or substrate. For example, the instructions may be printed on a substrate, such as paper or plastic, etc.

In some embodiments, the instructions may be present in the kit as a package insert, in the labeling of the container of the kit or components thereof (i.e., associated with the packaging or sub-packaging) etc. In other embodiments, the instructions are present as an electronic storage data file. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In some embodiments, the kit comprises an applier, configured to deliver a predefined amount of one or more of components (i) to (iii) to a solution or to a mixture thereof.

In some embodiments, the applier comprises a measuring tool allowing to measure the volume of each one of components (i) to (iii). In some embodiments, the measuring tool is automatically controlled. In some embodiments, the measuring tool is manually controlled.

According to some embodiments, the shelf life and/or the pot life of the matrix, the growth medium are long enough to allow them to be manufactured, stored and/or shipped to a user in a ready-for-use form, requiring no further process or preparation.

In some embodiments, the kit comprises a bacterial growth medium. In some embodiments, the kit comprises bacteria. In some embodiments, the bacterial growth medium comprises the bacteria.

In some embodiments, the bacterial growth medium comprises water. In some embodiments, the kit comprises water.

General

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1: Gelation Time Measurement

Pluronic® F-127 (sigma Aldrich Mo., USA) was dissolved in DDW in various concentrations: 14, 16, 18, and 20% (w/v). Each solution was dripped on 37° c plate and gelation time was measured (n=4). In order to examine the influence of the bacteria on Pluronic gelation time, same experiment was conducted for Pluronic solution 18% (w/v) mixed with Bacillus solution (in Luria-Bertani; LB).

In order to examine the influence of the bacteria on Pluronic gelation time, same experiment was conducted for pluronic solution 18% (w/v) mixed with Bacillus solution (in LB).

Pluronic, as thermo-sensitive polymer, exhibit a drastic and discontinuous change of the physical properties in response to temperature changing (FIG. 2A, 2B), in this study. The time that requires the polymer to solidify depends on it concentration. In this study, increasing Pluronic concentration from 14% (w/v) up to 20% (w/v) decreased the gelation time (FIG. 2C). In 20% (w/v) concentration the pluronic becomes gel in a few second, making the administration more difficult. In 14% (w/v) the solidification takes more than 15 min. that will cause the formulation to drip from the treated area. Hence, the optimal concentration that has been chosen is 18% (w/v), it enables both enough time for administration, but not too much time to solidify.

Adding another component to the polymer can result in gelation time changes. After the bacteria were added to the polymer, the gelation time was rechecked. It can be seen from the results (FIG. 2D) that the presence of the bacteria did not effect on the gelation time, the changes of the gelation time between the solutions were not statistically significant.

Example 2: Rheology Tests

In order to check the effect of the bacteria on Pluronic gelation temperature, the following solutions were examined in the rheometer: Pluronic solution (final concentration of 18% (w/v) in DDW), Pluronic solution 18% (w/v) mixed with Bacillus solution (10:1 respectively) and Pluronic solution 18% (w/v) mixed with LB solution (10:1 respectively). One ml of each solution (n=4) was dropped on DHR-3 Rheometer (TA Instruments, New Castle, Del., USA) stage. The method that was used was "temperature ramp"-G' was measured during stage heating from 4° C. to 45° C., frequency 1 rad/sec, 1% strain.

As a next step, it was important to check if the presence of the bacteria influence the gelation temperature. Using rheology analysis, G' was measured during changes of temperature from 4° C. to 45° C. In the results graph (FIG. 2E) it can be seen that all three curves, represent a different solution: Pluronic 18% (w/v), Pluronic 18% (w/v) with LB and Pluronic with bacteria (in LB), intersect at the same point, meaning, the bacteria do not affect the gelation point, the gelation temperature remains 37° C.

Example 3: Bacteria Viability Assay

The following solutions were prepared: Pluronic solution (final concentration of 18% (w/v) in DDW), Pluronic solution 18% (w/v) mixed with Bacillus solution (10:1 respectively), LB solution, LB solution mixed with bacteria solution (10:1 respectively), Pluronic solution 18% (w/v) mixed with LB solution (10:1 respectively). The solutions were incubated at 37° C. Samples were taken (n=3) in volume of 80µl from each solution and mixed with 80 µl BacTiter-Glo™ Microbial Cell Viability Assay kit (Promega, Wis., USA) into 96 well plates. Luminance was measured in Synergy™ H1 Plate reader (Biotech Instruments Inc., Winooski, Vt., USA).

In order to confirm that Pluronic can serve as protected medium for the bacteria, a viability assay was conducted. The kit consists of luciferin reagent, when it attached to an ATP molecule, its presence indicates live bacteria and it creates luminescence light. The luminescence was measured in plate reader. Pluronic was compared to LB which is the optimal medium for the bacteria to grow in. It can be seen in the graph (FIG. 3) that the bacteria grew in Pluronic at a smaller rate but in both solutions the peak is between $10^4$-$10^5$ ELU. So, we can conclude that Pluonic does not kill the bacteria.

Example 4: Skin Diffusion

Pluronic Substitution With Carboxyl

Pluronic (0.002 mol) was dissolve in anhydrous pyridine (Bio-Lab L.T.D Israel). The solution was heated to 50° c. Solid succinic anhydride (Bio-Lab L.T.D Israel) (4.8 mmol) was added over a period of several hours and the solution was stirred for another 8 hours. The pyridine solvent was evaporated. Remaining reactants were removed by dialysis against DDW using a membrane having a molecular weight cutoff of 1,000. The solution was lyophilized to get pluronic 127-COOH. Pluronic 127-COOH substitution with cyanine 3 amine: Pluronic 127-COOH solution (0.00008 mol in DDW) was mixed, dropwise in inert environment (N2), with cyanine 3 amine (Lumiprobe, Hallandale Beach, Fla., USA) solution (0.00000015 mol in DDW/DMSO (Merck, Germany) (1:1 volume). EDC (0.00024 mol in DDW/DMSO (1:1 volume)) and DMAP (0.00016 mol in DDW/DMSO (1:1 volume)) were added dropwise to the main solution. pH was set on 6.8 with NaOH. Remaining reactants were removed by dialysis against DDW using a membrane molecular weight cutoff of 1,000. The solution was lyophilized to get the final product, pluronic-cyanine 3 amine (FIG. 4A, FIG. 14).

Penetration experiment: Pig ears skin (were received from the Department of Medicine, Technion, Israel) were cut to 2×3 $cm^2$ samples. Pluronic-cyanine 3 amine (18% W/V) mixed with Syto-9 dye solution was administrated at 37° c on top of the skin at surface temperature of 37° C. in order to imitate the skin environment. The samples were incubated at 37° C. for 2 hours and then, were cut to circular 3mm diameter. The Samples were both examined in Confocal LSM 510 META Microscope (Carl Zeiss, Germany) to get the Z-stack images and also were freeze in Tissue-Plus O.C.T. (Scigen, Gardena, Calif.) for histology cuts and further observation in Eclipse Ti Microscope (Nikon Instruments Inc. Melville, N.Y., USA). (FIGS. 4B-4F)

The penetrability of the formula through the skin was measured ex vivo by applying 20 µL of the bacterial formula composed of synthesized fluorescently labeled Pluronic (FIG. 14) to fresh porcine ear skin (FIG. 4A). The formula was allowed to gel in situ at 37° C. and remained on the skin for an additional two hours before specimens were examined using confocal microscopy. The formula penetrated via the stratum corneum and accumulated in the epidermis (FIG. 4B), without penetrating the inner, dermis layer (FIG. 4C-F). The inventors note that the brightness of the fluorescence slightly decreased throughout the deeper skin layer, attributed to the aqueous nature of the hydrogel. Given that C. albicans infections are almost always confined to the upper portion of the epidermis, thus the penetrability of the formula is suitable for treating candida infections (e.g., candidiasis).

Example 5: Fungi Inhibition Area

Susceptibility test—in order to check which bacteria has the ability to inhibit different types of candida, 31 different types of Bacillus (in LB) were combined with 8 types of Candida. On each agar plate, one type of Candida was plated. On each plate 3 paper disc filters were located for 3 different concentration from the same bacteria, $10^7$, $10^8$, $10^9$ bac/ml. From each concentration, 10 µl were dripped on the paper disc. The plates were incubated for 48 hours and the inhibition radius was observed.

The first experiment was susceptibility test, 31 different types of Bacillus were combined with 8 types of Candida. The final results were presented in Table 1. To conclude, two types of Candida albicans were inhibited: Candida albicans haploid was inhibited by 10 types of *Bacillus* and Candida albicans diploid was inhibited by 5 types of *Bacillus*.

TABLE 1

Inhibition activity of different types of Bacillus on two types of Candida

|  |  | Candida Albicans Haploid | Candida Albicans Diploid |
|---|---|---|---|
| Bacillus subtilis RO-A-4 | $10^7$ bac/ml | — | 1 |
|  | $10^8$ bac/ml | — | 1 |
|  | $10^9$ bac/ml | — | 2 |
| Bacillus PS | $10^7$ bac/ml | 1 | 1 |
|  | $10^8$ bac/ml | 2 | 1 |
|  | $10^9$ bac/ml | 1 | 2 |
| Bacillus subtilis RO-NN-1 | $10^7$ bac/ml | 2 | — |
|  | $10^8$ bac/ml | 1 | — |
|  | $10^9$ bac/ml | 3 | — |
| Bacillus subtilis RO-FF-1 | $10^7$ bac/ml | 2 | — |
|  | $10^8$ bac/ml | 3 | — |
|  | $10^9$ bac/ml | 3 | — |
| Bacillus mojavenesis RO-B-2 | $10^7$ bac/ml | 2 | 1 |
|  | $10^8$ bac/ml | 1 | 1 |
|  | $10^9$ bac/ml | 2 | 1 |
| Basillus subtilis AUSI98 | $10^7$ bac/ml | 1 | — |
|  | $10^8$ bac/ml | 2 | — |
|  | $10^9$ bac/ml | 3 | — |
| Bacillis licheniformis 749/C | $10^7$ bac/ml | 1 | 1 |
|  | $10^8$ bac/ml | 1 | 1 |
|  | $10^9$ bac/ml | 2 | 1 |
| Licheniformis EI-34-06 | $10^7$ bac/ml | 1 | — |
|  | $10^8$ bac/ml | 3 | — |
|  | $10^9$ bac/ml | 3 | — |
| Bacillus subtilis 3610 | $10^7$ bac/ml | 1 | 1 |
|  | $10^8$ bac/ml | 1 | 1 |
|  | $10^9$ bac/ml | 2 | 1 |
| Basillus subtilis RS-D-2 | $10^7$ bac/ml | 1 | — |
|  | $10^8$ bac/ml | 2 | — |
|  | $10^9$ bac/ml | 2 | — |
| Bacillus amyloliquefaciens subsp. plantarum FZB42T | $10^7$ bac/ml | 3 | — |
|  | $10^8$ bac/ml | 3 | — |
|  | $10^9$ bac/ml | 3 | — |

See Index numbers 1-3 in FIG. 5

*Candida Albicans* diploid inhibition with *Bacillus subtilis* 3610—On each agar plate, Candida Albicans diploid solution was plated. On each plate (n=3) paper disc filter was located. 10 µl of Pluronic-Bacillus subtilis 3610 solution were dripped on the paper disc. The plates were incubated for 48 hours and the inhibition radius was observed.

The same experiment was conducted with Surfacrin and Ketoconazole (FIGS. 7, and 8B).

Example 6: Surfactin Extract

Surfactin extraction from LB: Bacteria were grown in optimized medium: Sucrose 20 g, Peptone 30 g, Yeast extract 7 g, KH2 PO4 1.9 g, MgSO4 0.450 g per liter of distilled water. The medium was centrifuge, HCl was added to reach pH=2 creating white precipitate. The precipitate was dissolved in PBS, pH=8 (using NaOH). The solution was measured in HPLC (80:20 (volume) Acetonitrile: Trifluoroacetic acid) along with commercial surfactin solutions at 8 different concentrations: ,0.004, 0.02, 0.1, 0.5, 1 0.000032, 0.00016, 0.0008 gr/ml (FIG. 8A).

Surfactin extraction from formula and determination in LC-MS: *B. subtilis* was grown in the formula (90% pluronic/10% LB) for 6 h at 37° C. The bacteria and pluronic solution were subsequently removed from the medium by centrifugation at 8,000 g for 10 min. The supernatant fluid was adjusted to pH 2.0 using 6 M HCl and allowed to precipitate at 4° C. overnight. The precipitate was centrifuged at 11,000 g for 20 min and the pellet was dissolved in DDW, lyophilized and re-dissolved in acetonitrile: DDW (80:20) before quantitative analysis by LC-MS was carried out using a modified reported method. Analysis of the surfactin was performed on a Waters UPLC H-class system equipped with a Waters Acquity C18 column (50 mm×2.1 mm, 2.6 µm particle; Injection volume 7 µL). The mobile phase consisted of solvent A (DDW containing 0.1% Trifluoroacetic acid) and solvent B (acetonitrile containing 0.1% Trifluoroacetic acid). The following linear gradient elution was used: 50% A at 0 min, decreased to 3% A from 0 to 10 min, held at 3% A from 10 to 12 min, then increased to 50% A from 12 to 12.5 min, and further held at 50% A until 17 min. The flow rate was set at 0.4 ml/min and the effluent was monitored by the absorbance at 210 nm.

Example 7: Candida Inhibition Area

The antifungal activity of five B. strains (in LB) was tested against C albicans SC5314 (YJB-T1). C. albicans samples (0.1 ml, 0.02 OD at 600 nm in DDW) were plated onto yeast extract peptone dextrose (YPD). Then, three paper disks (6 mm diameter, Becton, Dickinson and Company, USA) were placed at the center of each plate followed by loading with 10 µl of bacteria at concentrations of $10^7$, $10^8$ or $10^9$ bac/ml. After 48 h of incubation at 30° C., the zones of inhibition were measured using a millimeter scale. Inhibition by ketoconazole was carried out in the same manner using ethylene glycol as a solvent and as a negative control. Similarly, surfactin was dissolved in a Tris buffer solution (1 mg/ml) and ethylene glycol at 0.2 mg/ml.

Susceptibility test—in order to check which bacteria has the ability to inhibit candida, five different types of *Bacillus* (in LB) were combined with *Candida albicans* YJB T1. On each agar plate 3 paper disc filters were located for 3 different concentrations of the same bacteria, $10^7$, $10^8$, $10^9$ bac/ml. From each concentration, 10 µl were dripped onto the paper disc. The plates were incubated for 48 hours and the inhibition radius was observed.

TABLE 2

Inhibition activity of different types of *Bacillus subtilis* on *Candida*.

| Bacillus subtilis Strain | Conc. (bac/ml) | Zone of inhibition (mm) |
|---|---|---|
| Bacillus subtilis 3610 | $10^7$ | 10.6 ± 0.4 |
|  | $10^8$ | 10.8 ± 0.6 |
|  | $10^9$ | 11.4 ± 0.2 |
| Bacillus PS | $10^7$ | 8.0 ± 0.1 |
|  | $10^8$ | 8.8 ± 0.2 |
|  | $10^9$ | 13.4 ± 0.3 |
| Bacillus mojavenesis RO-B-2 | $10^7$ | 9.8 ± 0.2 |
|  | $10^8$ | 10.6 ± 0.4 |
|  | $10^9$ | 12.2 ± 0.2 |
| Bacillus lichcniformis 749/C | $10^7$ | 12.0 ± 0.2 |
|  | $10^8$ | 12.6 ± 0.6 |
|  | $10^9$ | 16 ± 0.8 |
| Bacillus subtilis RO-A-4 | $10^7$ | 10.6 ± 0.4 |
|  | $10^8$ | 11.8 ± 0.2 |
|  | $10^9$ | 13.2 ± 0.3 |

*B. subtilis* 3610 was chosen as the optimal strain based on a tradeoff between its activity and the fact that it is the natural wild type, non-modified strain (FIGS. 9A-B).

Example 8: Gelation Properties And Characterization

Reversible transformation of a Pluronic F-127 solution (18% w/v) was evaluated. Pluronic has a lower critical solution temperature (LCST), around body temperature (FIG. 10A).

The insertion of LB and bacteria, slightly increased the storage modulus (G') at the solution state and reduces it at the gel state; this is attributable to the binding of solute molecules to the Pluronic chains. Nevertheless, the incorporation of LB and bacteria into the pluronic solution had no significant effect on gelation time and on the reversibility of the sol-gel transition (FIG. 10B). Storage and loss moduli, however, increased slightly compared with their initial values, after a single heating/cooling cycle. Taking together, rheology experiments implied that an 18% w/v Pluronic formula, containing 10% v/v bacteria in LB media, would be user-friendly with minimal chance of drainage from the site of application, leading to a prolonged retention of B. subtilis on the skin.

Example 9: Antifungal Activity

The antifungal activity of the bacillus ($10^8$/ml) in the formula was determined using the disk diffusion method and was compared to that of empty formulation (without bacillus) and of ketoconazole 2% w/v in ethylene glycol (FIG. 11). A lawn of C. albicans (100 µl of $10^7$ cells/ml) was spread on yeast extract-peptone-dextrose (YPD) agar petri dishes and tested solutions (10 µl ) were loaded on paper filter disks (6 mm in diameter) placed at the center of each dish and incubated at 37° C. for 48 h. The bacillus formula demonstrated antifungal activity comparable to the ketoconazole (diameter inhibition zones were 12 and 14 mm, correspondingly, p>0.05), while the control formula did not exhibit antifungal activity (FIG. 11).

The antifungal activity of B. subtilis against C. albicans was potentially due to several factors. One was the release of surfactin, the most powerful biosurfactant that possesses a broad antifungal activity. High-performance liquid chromatography (HPLC) analysis (FIG. 8A) confirmed the presence of surfactin in the bacterial formulation, consistent with the idea that surfactin plays a constructive role in the observed antifungal activity. Moreover, B. cells were cultivated in the formula (90% pluronic/10% LB) for 6 h and surfactin concentrations were sampled by LC-MS (FIG. 12B and FIG. 13). B. subtillis produced surfactin mixtures, comprising homologues protonated molecules [M+H]+ at m/z 994, 1008, 1022, 1036 and 1050, consistent with standard surfactin isomers with side chains of different lengths (C12, C13, C14, C15, and C16, respectively) (FIG. 12B). Surfactin C15 concentrations increased over the first 3 h then remained constant at 12 µg/mL (FIG. 13). These results confirmed that our formula produced high concentrations of C15 surfactin, exceeding the reported synergistic anti-fungal MIC value of 6.25 µg/mL.

Example 10: Cutaneous Fungal Infection

In vivo: Preparation of C. albicans culture: C. albicans were cultured overnight in a YPD agar while shaken at 30° C. A C. albicans suspension was diluted in YPD ($10^9$ bac/ml) and 50 µl of this mixture were diluted 1:100 with a YPD broth containing 10% FBS, to a final concentration of $10^7$ bac/ml (O.D. 0.01 at 600 nm). The solution was incubated at 37° C. for two hours to induce a hyphal formation. The suspension was centrifuged and the pellet was washed with PBS three times.

Animal protocol: Animals were cared for in compliance with protocols approved by the Council for Animal Experiments, Israel Ministry of Health, in conformity with the Animal Welfare law guidelines (published in 1994). Forty eight six-week-old C57BL/6 mice (Envigo, Jerusalem, Israel) were anesthetized by an intraperitoneal (i.p.) injection of ketamine (100 mg/kg) and xylazine (20 mg/kg). The dorsal region was carefully shaved and an intradermal injection of 50 µl candida culture (see paragraph above) was performed using a 25G needle. After 48 h, mice were randomly assigned to one of each group: pure Pluronic, Pluronic containing B. subtilis ($10^8$ bac/ml), ketoconazole cream (Nizoral 20 mg/g, Janssen, Switzerland) and a control group that did not receive any treatment ("no treatment"). Each treatment was administered daily for the entire period of the experiment. Mice were sacrificed after 4 or 10 days and the dorsal skin sample was harvested and kept in 4% formalin for histology analysis. Skin samples were stained with hematoxilin and eosin for histology evaluation.

The histological evaluation of the skin pertaining to treatment sites was made by a subjective description of the observed tissue reaction, based on parameters describing grades of tissue tolerance (i.e., inflammation and fibrosis). The scoring of the lesions was done semi-quantitatively, using a 5-point grading scale (0 to 4), taking into consideration the severity of the changes (0=no change, 1=minimal change, 2=mild change, 3=moderate change, 4=marked change).

Figure 15I:
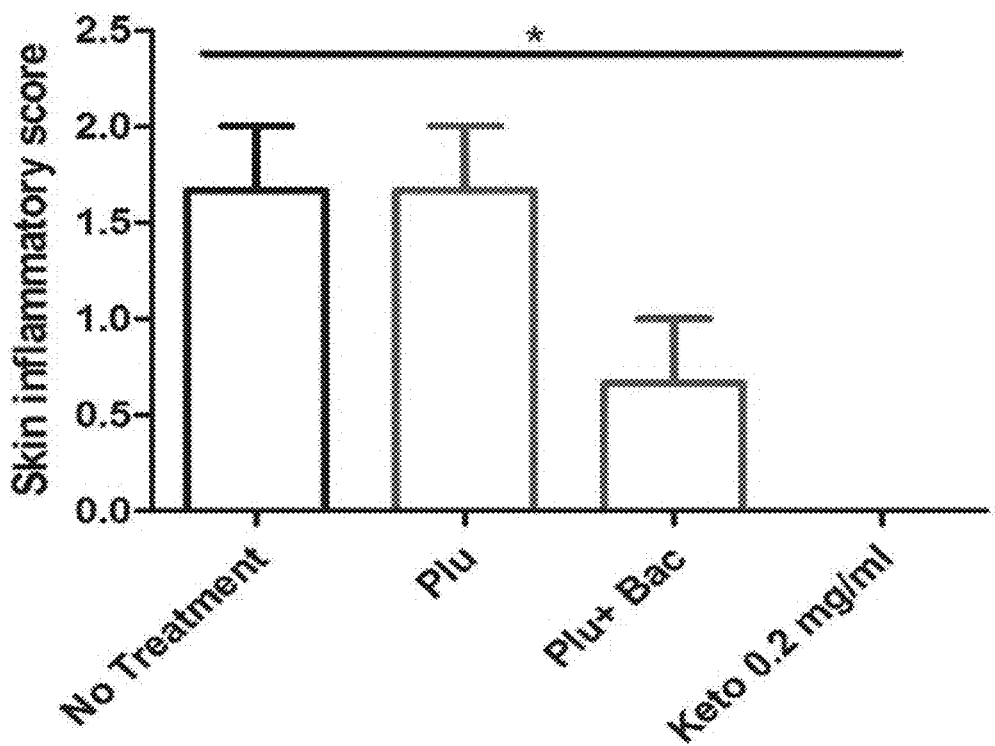

The efficacy of the bacillus formulation was evaluated in vivo using a cutaneous fungal infection model. Infection was induced by intradermally injecting C. albicans pseudohyphae (50 µl , 5×$10^7$, hyphal formation) into the dorsal region of 48 C57BL/6 mice (Envigo, Jerusalem, Israel). After 48 h, mice were randomly assigned to one of 4 groups (6 mice per group): pure 18% Pluronic, 18% Pluronic containing B. subtilis ($10^8$ bac/ml), ketoconazole cream (Nizoral® 20 mg/g, Janssen, Switzerland) and a negative control not receiving any treatment (no treatment). Each treatment was administered once daily for the duration of the experiment. Mice were sacrificed on days 4 and 10, and histological evaluation, based on a scoring system ranging from 0-4 was made on skin and underlying subcutaneous tissue samples extracted from the area of infection. After four days of treatment, control mice ("no treatment") and pure Pluronic gel groups (FIG. 15A and FIG. 15B, correspondingly) developed a subacute inflammation with an average inflammation score of 1.7 (FIG. 15I). Both inflammations were characterized by polymorphonuclear and mononuclear cells, intermixed with fibroblastic proliferation and scant collagen deposition. In contrast, mice treated with the B. subtilis formulation or with ketoconazole ointment (FIG. 15C and FIG. 15D) had minimal subacute inflammation, with average scores of 0.6 and 0, respectively FIG. 15I).

Figure 15J:
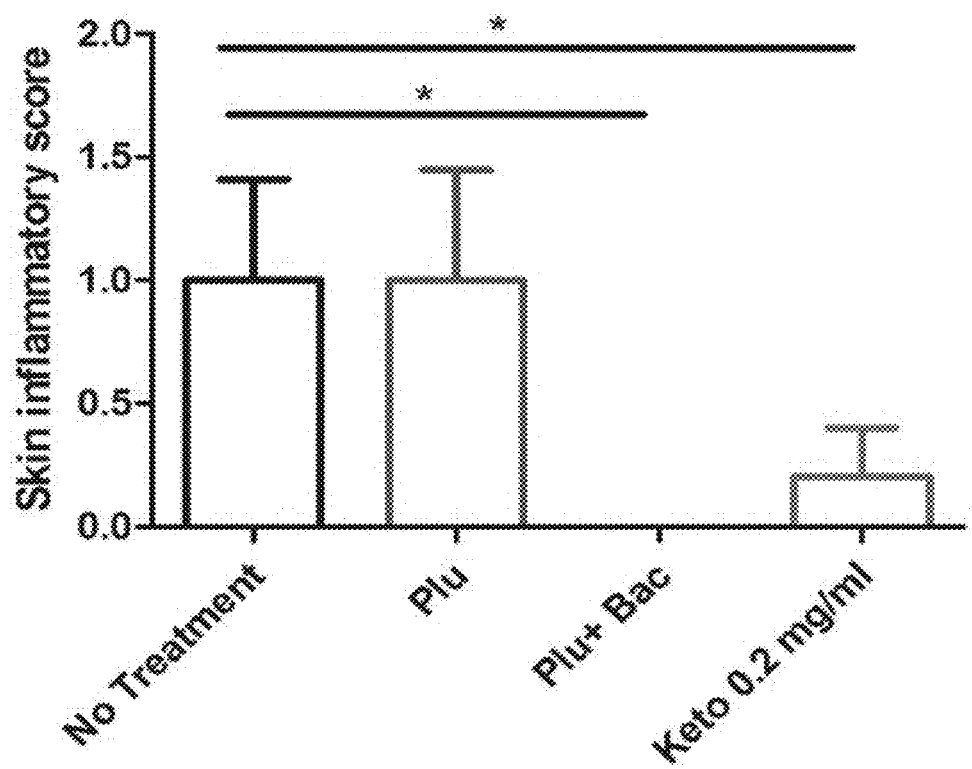

After 10 days, control and Pluronic gel groups still demonstrated acute inflammation (FIG. 15E and FIG. 15F, correspondingly). Inflammation was characterized by collections of polymorphonuclear cells with an average score of 1 (FIG. 15J). By contrast, after 10 days, no inflammation was detected in mice treated with the B. subtilis formulation (FIG. 15G and FIG. 15J), scored 0. Mice treated with ketoconazole (FIG. 15E) displayed minimal evidence of chronic inflammatory predominated by fibroblastic proliferation, collagen deposition and interspersed mixed mononuclear cells (FIG. 15H) with an average inflammation score of 0.2 (FIG. 15J). These in vivo results generally mirrored the results seen in vitro (FIG. 15B): The B. subtilis and ketoconazole formulations inhibited candida growth while the carrier, the 18% Pluronic solution, had no effect. Thus, the in vivo study supports the idea a living bacterial formulation may be effective in treating local fungal infections.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A kit comprising:
   (i) a material characterized by a viscosity that is less than about 1 Pa under a first stimulus, and a viscosity that is higher than about 100 Pa under a second stimulus;
   (ii) a bacterial growth medium; and
   (iii) a population of non-pathogenic viable bacteria, wherein said first stimulus comprises a temperature below 35° C., and said second stimulus comprises a temperature above 36° C.; and wherein said material is characterized by a gelation time between 30 sec to 15 min.

2. The kit of claim 1, wherein said first stimulus and said second stimulus are selected from the group consisting of temperature, and pH.

3. The kit of claim 1, wherein said material is a reverse thermo-responsive material.

4. The kit of claim 1, wherein said material is characterized by lower critical solution temperatures (LCST).

5. The kit of claim 1, wherein said material is a polymeric material.

6. The kit of claim 5, wherein said polymeric material is selected from poly(ethylene oxide)-poly(propylene oxide)-poly(ethylene oxide) (PEO-PPO-PEO) triblocks, random or alternating reverse thermo-responsive PEO-PPO block copolymers, and copolymers comprising PEO and PPO segments.

7. The kit of claim 1, wherein the population of said non-pathogenic viable bacteria is selected from a population of non-pathogenic bacteria resident on the skin or a mucous membrane of a mammal.

8. The kit of claim 7, wherein the non-pathogenic viable bacteria have a therapeutic or cosmetic effect.

9. The kit of claim 1, wherein said bacteria comprise at least one of *Acinetobacter, Actinomycetales, Anaerococcus, Bacillales, Bifidobacterium, Enhydrobacter, Enterococcus, Finegoldia, Carnobacterium, Coryneobacterium, Lactobacillus, Lactococcus, Leunconostoc, Macrooccus, Micrococcineae, Oenococcus, Pediococcus, Peptoniphilus, Propionibacterium, Salinicoccus, Sphingomonas, Streptococcus, Tetragenoccus, Weissella, Bacillus Subtilis, Bacillus uniflagellatus, Bacillus lateropsorus, Bacillus laterosporus* BOD, *Bacillus megaterium, Bacillus polymyxa, Bacillus lichenifonnis, Bacillus pumilus, Bacillus sterothermophilus, Lactobacillus casei, Lactobacillus reuteri, Lactobacillus acidophilus, Lactobacillus jensenii, Bifidobacterium lognum, Bifidobacterium reuteri, Bifidobacterium lactis, Bifidobacterium breve, Bifidobacterium animalis, Propionibacterium acidipropionici, Propionibacterium freudenreichii, Propionibacterium thoenii,* and *Propionibacterium jensenii.*

10. A kit comprising a material characterized by a viscosity that is less than about 1 Pa under a first stimulus, and a viscosity that is higher than about 100 Pa under a second stimulus; and a population of non-pathogenic viable bacteria, wherein said first stimulus comprises a temperature below 35° C., and said second stimulus comprises a temperature above 36° C.; wherein said material is characterized by a gelation time between 30 sec to 15 min; wherein said material is a hydrogel comprising a polymer and a bacterial growth medium; and wherein the non-pathogenic viable bacteria inhibit growth of pathogenic-bacteria, yeast, fungus or virus.

11. The kit of claim 10, wherein said non-pathogenic viable bacteria are probiotic bacteria, and wherein said kit comprises instructions for incorporating the non-pathogenic viable bacteria into said hydrogel.

12. The kit of claim 1, further comprising an applier, configured to deliver a predefined amount of one or more of components (i) to (iii) to a solution or to a mixture thereof.

* * * * *